US 8,200,341 B2

(12) United States Patent
Sanghera et al.

(10) Patent No.: US 8,200,341 B2
(45) Date of Patent: Jun. 12, 2012

(54) SENSING VECTOR SELECTION IN A CARDIAC STIMULUS DEVICE WITH POSTURAL ASSESSMENT

(75) Inventors: Rick Sanghera, Fullerton, CA (US); Venugopal Allavatam, Oceanside, CA (US)

(73) Assignee: Cameron Health, Inc., San Clemente, CA (US)

( * ) Notice: Subject to any disclaimer, the term of this patent is extended or adjusted under 35 U.S.C. 154(b) by 976 days.

(21) Appl. No.: 11/672,353

(22) Filed: Feb. 7, 2007

(65) Prior Publication Data

US 2008/0188901 A1    Aug. 7, 2008

(51) Int. Cl.
*A61N 1/00* (2006.01)
*A61B 5/04* (2006.01)

(52) U.S. Cl. .............. 607/116; 607/2; 607/38; 600/508; 600/522

(58) Field of Classification Search ................ 607/2, 38, 607/116; 600/508, 522
See application file for complete search history.

(56) References Cited

U.S. PATENT DOCUMENTS

| | | | |
|---|---|---|---|
| 3,653,387 A | 4/1972 | Ceier | |
| 3,710,374 A | 1/1973 | Kelly | |
| 3,911,925 A | 10/1975 | Tillery, Jr. | |
| 4,030,509 A | 6/1977 | Heilman et al. | |
| 4,157,720 A | 6/1979 | Greatbatch | |
| 4,164,946 A | 8/1979 | Langer | |
| 4,184,493 A | 1/1980 | Langer et al. | |
| 4,191,942 A | 3/1980 | Long | |
| 4,210,149 A | 7/1980 | Heilman et al. | |
| RE30,387 E | 8/1980 | Denniston, III et al. | |
| 4,223,678 A | 9/1980 | Langer et al. | |
| 4,248,237 A | 2/1981 | Kenny | |
| 4,254,775 A | 3/1981 | Langer | |
| 4,291,707 A | 9/1981 | Heilman et al. | |
| 4,300,567 A | 11/1981 | Kolenik et al. | |
| 4,314,095 A | 2/1982 | Moore et al. | |
| 4,375,817 A | 3/1983 | Engle et al. | |
| 4,402,322 A | 9/1983 | Duggan | |
| 4,407,288 A | 10/1983 | Langer et al. | |
| 4,424,818 A | 1/1984 | Doring et al. | |
| 4,450,527 A | 5/1984 | Sramek | |
| 4,548,209 A | 10/1985 | Wielders et al. | |
| 4,550,502 A | 11/1985 | Grayzel | |
| 4,567,900 A | 2/1986 | Moore | |

(Continued)

FOREIGN PATENT DOCUMENTS

DE    29801807    7/1998

(Continued)

OTHER PUBLICATIONS

International Search Report for PCT/US2008/053197; published Aug. 14, 2008 as part of WO/2008/098062.

(Continued)

*Primary Examiner* — Nicole F Lavert
(74) *Attorney, Agent, or Firm* — Pramudji Law Group PLLC; Ari Pramudji; Mark Schroeder

(57) ABSTRACT

Methods, implantable medical devices and systems configured to perform analysis of captured signals from implanted electrodes to identify cardiac arrhythmias. In an illustrative embodiment, signals captured from two or more sensing vectors are analyzed, where the signals are captured with a patient in at least first and second body positions. Analysis is performed to identify primary or default sensing vectors and/or templates for event detection.

9 Claims, 15 Drawing Sheets

U.S. PATENT DOCUMENTS

| | | | |
|---|---|---|---|
| 4,589,420 A | 5/1986 | Adams et al. | |
| 4,595,009 A | 6/1986 | Leinders | |
| 4,602,637 A | 7/1986 | Elmqvist et al. | |
| 4,603,705 A | 8/1986 | Speicher et al. | |
| 4,693,253 A | 9/1987 | Adams | |
| 4,727,877 A | 3/1988 | Kallok | |
| 4,750,494 A | 6/1988 | King | |
| 4,765,341 A | 8/1988 | Mower et al. | |
| 4,768,512 A | 9/1988 | Imran | |
| 4,800,883 A | 1/1989 | Winstrom | |
| 4,830,005 A | 5/1989 | Woskow | |
| 4,944,300 A | 7/1990 | Saksena | |
| 5,044,374 A | 9/1991 | Lindemans et al. | |
| 5,105,810 A | 4/1992 | Collins et al. | |
| 5,105,826 A | 4/1992 | Smits et al. | |
| 5,109,842 A | 5/1992 | Adinolfi | |
| 5,129,392 A | 7/1992 | Bardy et al. | |
| 5,133,353 A | 7/1992 | Hauser | |
| 5,137,025 A | 8/1992 | Turner, II | |
| 5,144,946 A | 9/1992 | Weinberg et al. | |
| 5,184,616 A | 2/1993 | Weiss | |
| 5,191,901 A | 3/1993 | Dahl et al. | |
| 5,203,348 A | 4/1993 | Dahl et al. | |
| 5,215,081 A | 6/1993 | Ostroff | |
| 5,230,337 A | 7/1993 | Dahl et al. | |
| 5,255,692 A | 10/1993 | Neubauer et al. | |
| 5,261,400 A | 11/1993 | Bardy | |
| 5,271,411 A | 12/1993 | Ripley et al. | |
| 5,291,895 A | 3/1994 | McIntyre | |
| 5,299,119 A * | 3/1994 | Kraf et al. | 600/509 |
| 5,300,106 A | 4/1994 | Dahl et al. | |
| 5,313,953 A | 5/1994 | Yomtov et al. | |
| 5,331,966 A | 7/1994 | Bennett et al. | |
| 5,342,407 A | 8/1994 | Dahl et al. | |
| 5,366,496 A | 11/1994 | Dahl et al. | |
| 5,370,667 A | 12/1994 | Alt | |
| 5,376,103 A | 12/1994 | Anderson et al. | |
| 5,376,104 A | 12/1994 | Sakai et al. | |
| 5,385,574 A | 1/1995 | Hauser et al. | |
| 5,391,200 A | 2/1995 | KenKnight et al. | |
| 5,405,363 A | 4/1995 | Kroll et al. | |
| 5,411,539 A | 5/1995 | Neisz | |
| 5,411,547 A | 5/1995 | Causey, III | |
| 5,413,591 A | 5/1995 | Knoll | |
| 5,423,326 A | 6/1995 | Wang et al. | |
| 5,431,693 A | 7/1995 | Schroeppel | |
| 5,439,485 A | 8/1995 | Mar et al. | |
| 5,441,518 A | 8/1995 | Adams et al. | |
| 5,447,521 A | 9/1995 | Anderson et al. | |
| 5,476,503 A | 12/1995 | Yang | |
| 5,501,702 A | 3/1996 | Plicchi et al. | |
| 5,509,923 A | 4/1996 | Middleman et al. | |
| 5,509,928 A | 4/1996 | Acken | |
| 5,531,765 A | 7/1996 | Pless | |
| 5,531,766 A | 7/1996 | Kroll et al. | |
| 5,534,019 A | 7/1996 | Paspa | |
| 5,534,022 A | 7/1996 | Hoffmann et al. | |
| 5,540,727 A | 7/1996 | Tockman et al. | |
| 5,558,098 A | 9/1996 | Fain | |
| 5,597,956 A | 1/1997 | Ito et al. | |
| 5,601,607 A | 2/1997 | Adams | |
| 5,603,732 A | 2/1997 | Dahl et al. | |
| 5,607,455 A | 3/1997 | Armstrong | |
| 5,618,287 A | 4/1997 | Fogarty et al. | |
| 5,620,477 A | 4/1997 | Pless et al. | |
| 5,643,328 A | 7/1997 | Cooke et al. | |
| 5,645,586 A | 7/1997 | Meltzer | |
| 5,658,317 A | 8/1997 | Haefner et al. | |
| 5,658,319 A | 8/1997 | Kroll | |
| 5,658,321 A | 8/1997 | Fayram et al. | |
| 5,674,260 A | 10/1997 | Weinberg | |
| 5,690,648 A | 11/1997 | Fogarty et al. | |
| 5,690,683 A | 11/1997 | Haefner et al. | |
| 5,697,953 A | 12/1997 | Kroll et al. | |
| 5,713,926 A | 2/1998 | Hauser et al. | |
| 5,766,226 A | 6/1998 | Pedersen | |
| 5,776,169 A | 7/1998 | Schroeppel | |
| 5,814,090 A | 9/1998 | Latterell et al. | |
| 5,827,326 A | 10/1998 | Kroll et al. | |
| 5,836,976 A | 11/1998 | Min et al. | |
| 5,843,132 A | 12/1998 | Ilvento | |
| 5,895,414 A | 4/1999 | Sanchez-Zambrano | |
| 5,904,705 A | 5/1999 | Kroll et al. | |
| 5,919,211 A | 7/1999 | Adams | |
| 5,919,222 A | 7/1999 | Hjelle et al. | |
| 5,925,069 A | 7/1999 | Graves et al. | |
| 5,935,154 A | 8/1999 | Westlund | |
| 5,941,904 A | 8/1999 | Johnston et al. | |
| 5,957,956 A | 9/1999 | Kroll et al. | |
| 5,987,352 A * | 11/1999 | Klein et al. | 600/509 |
| 5,999,853 A | 12/1999 | Stoop et al. | |
| 6,014,586 A | 1/2000 | Weinberg et al. | |
| 6,026,325 A | 2/2000 | Weinberg et al. | |
| 6,029,086 A | 2/2000 | Kim et al. | |
| 6,044,297 A | 3/2000 | Sheldon et al. | |
| 6,058,328 A | 5/2000 | Levine et al. | |
| 6,093,173 A | 7/2000 | Balceta et al. | |
| 6,095,987 A | 8/2000 | Shmulewitz et al. | |
| H1905 H | 10/2000 | Hill | |
| 6,128,531 A | 10/2000 | Campbell-Smith | |
| 6,144,866 A | 11/2000 | Miesel et al. | |
| 6,144,879 A | 11/2000 | Gray | |
| 6,148,230 A | 11/2000 | KenKnight | |
| 6,185,450 B1 | 2/2001 | Seguine et al. | |
| 6,190,324 B1 | 2/2001 | Kieval et al. | |
| 6,266,554 B1 | 7/2001 | Hsu et al. | |
| 6,266,567 B1 | 7/2001 | Ishikawa et al. | |
| 6,278,894 B1 | 8/2001 | Salo et al. | |
| 6,280,462 B1 | 8/2001 | Hauser et al. | |
| 6,308,095 B1 | 10/2001 | Hsu et al. | |
| 6,334,071 B1 | 12/2001 | Lu | |
| 6,345,198 B1 | 2/2002 | Mouchawar et al. | |
| 6,411,844 B1 | 6/2002 | Kroll et al. | |
| 6,490,486 B1 | 12/2002 | Bradley | |
| 6,493,579 B1 | 12/2002 | Gilkerson et al. | |
| 6,493,584 B1 | 12/2002 | Lu | |
| 6,496,715 B1 | 12/2002 | Lee et al. | |
| 6,516,225 B1 | 2/2003 | Florio | |
| 6,567,691 B1 | 5/2003 | Stadler | |
| 6,574,505 B1 | 6/2003 | Warren | |
| 6,625,490 B1 | 9/2003 | McClure et al. | |
| 6,647,292 B1 | 11/2003 | Bardy et al. | |
| 6,658,292 B2 | 12/2003 | Kroll et al. | |
| 6,684,100 B1 | 1/2004 | Sweeney et al. | |
| 6,687,540 B2 | 2/2004 | Marcovecchio | |
| 6,699,200 B2 | 3/2004 | Cao et al. | |
| 6,708,062 B2 | 3/2004 | Ericksen et al. | |
| 6,721,597 B1 | 4/2004 | Bardy et al. | |
| 6,728,572 B2 | 4/2004 | Hsu et al. | |
| 6,731,978 B2 | 5/2004 | Olson et al. | |
| 6,738,667 B2 | 5/2004 | Deno et al. | |
| 6,751,502 B2 | 6/2004 | Daum et al. | |
| 6,754,528 B2 | 6/2004 | Bardy et al. | |
| 6,778,860 B2 | 8/2004 | Ostroff et al. | |
| 6,788,974 B2 | 9/2004 | Bardy et al. | |
| 6,810,284 B1 | 10/2004 | Bradley | |
| 6,834,204 B2 | 12/2004 | Ostroff et al. | |
| 6,856,835 B2 | 2/2005 | Bardy et al. | |
| 6,865,417 B2 | 3/2005 | Rissmann et al. | |
| 6,866,044 B2 | 3/2005 | Bardy et al. | |
| 6,892,092 B2 | 5/2005 | Palreddy et al. | |
| 6,909,916 B2 | 6/2005 | Spinelli et al. | |
| 6,927,721 B2 | 8/2005 | Ostroff | |
| 6,937,907 B2 | 8/2005 | Bardy et al. | |
| 6,950,705 B2 | 9/2005 | Bardy et al. | |
| 6,952,608 B2 | 10/2005 | Ostroff | |
| 6,952,610 B2 | 10/2005 | Ostroff et al. | |
| 6,954,670 B2 | 10/2005 | Ostroff | |
| 6,959,212 B2 | 10/2005 | Hsu et al. | |
| 6,975,904 B1 | 12/2005 | Sloman | |
| 6,980,856 B2 | 12/2005 | Sullivan et al. | |
| 6,988,003 B2 | 1/2006 | Bardy et al. | |
| 6,993,379 B1 | 1/2006 | Kroll et al. | |
| 6,996,434 B2 | 2/2006 | Marcovecchio et al. | |
| 7,016,730 B2 | 3/2006 | Ternes | |
| 7,020,523 B1 | 3/2006 | Lu et al. | |
| 7,027,858 B2 | 4/2006 | Cao et al. | |

| | | | |
|---|---|---|---|
| 7,027,862 B2 | 4/2006 | Dahl et al. | |
| 7,031,764 B2 | 4/2006 | Schwartz et al. | |
| 7,039,459 B2 | 5/2006 | Bardy et al. | |
| 7,039,463 B2 | 5/2006 | Marcovecchio | |
| 7,039,465 B2 | 5/2006 | Bardy et al. | |
| 7,043,299 B2 | 5/2006 | Erlinger et al. | |
| 7,062,329 B2 | 6/2006 | Ostroff | |
| 7,065,407 B2 | 6/2006 | Bardy et al. | |
| 7,065,410 B2 | 6/2006 | Bardy et al. | |
| 7,069,080 B2 | 6/2006 | Bardy et al. | |
| 7,076,294 B2 | 7/2006 | Bardy et al. | |
| 7,076,296 B2 | 7/2006 | Rissmann et al. | |
| 7,090,682 B2 | 8/2006 | Sanders et al. | |
| 7,092,754 B2 | 8/2006 | Bardy et al. | |
| 7,120,495 B2 | 10/2006 | Bardy et al. | |
| 7,120,496 B2 | 10/2006 | Bardy et al. | |
| 7,130,689 B1 | 10/2006 | Turcott | |
| 7,146,212 B2 | 12/2006 | Bardy et al. | |
| 7,149,575 B2 | 12/2006 | Ostroff et al. | |
| 7,167,747 B2 | 1/2007 | Gunderson et al. | |
| 7,181,274 B2 | 2/2007 | Rissmann et al. | |
| 7,181,281 B1 | 2/2007 | Kroll | |
| 7,266,409 B2 | 9/2007 | Gunderson | |
| 7,366,569 B2 | 4/2008 | Belalcazar | |
| 7,412,287 B2 | 8/2008 | Yonce et al. | |
| 2001/0034487 A1 | 10/2001 | Cao et al. | |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035381 A1 | 3/2002 | Bardy et al. | |
| 2002/0095184 A1 | 7/2002 | Bardy et al. | |
| 2002/0107544 A1 | 8/2002 | Ostroff et al. | |
| 2002/0107545 A1 | 8/2002 | Rissmann et al. | |
| 2002/0169484 A1 | 11/2002 | Mathis et al. | |
| 2003/0088277 A1 | 5/2003 | Ostroff | |
| 2004/0230243 A1 | 11/2004 | Haefner et al. | |
| 2004/0254611 A1 | 12/2004 | Palreddy et al. | |
| 2004/0254613 A1 | 12/2004 | Ostroff et al. | |
| 2005/0049644 A1 | 3/2005 | Warren et al. | |
| 2005/0192505 A1* | 9/2005 | Ostroff et al. | 600/509 |
| 2006/0085038 A1 | 4/2006 | Linder et al. | |
| 2006/0116595 A1 | 6/2006 | Palreddy et al. | |
| 2006/0122676 A1 | 6/2006 | Ko et al. | |
| 2006/0167502 A1 | 7/2006 | Haefner | |
| 2006/0173498 A1 | 8/2006 | Banville et al. | |
| 2007/0123947 A1 | 5/2007 | Wenger et al. | |
| 2007/0232944 A1 | 10/2007 | Ghanem et al. | |
| 2007/0232945 A1 | 10/2007 | Kleckner et al. | |
| 2007/0232948 A1 | 10/2007 | Stadler et al. | |
| 2007/0233196 A1 | 10/2007 | Stadler et al. | |
| 2007/0233198 A1 | 10/2007 | Ghanem et al. | |
| 2007/0239044 A1 | 10/2007 | Ghanem et al. | |
| 2007/0239045 A1 | 10/2007 | Ghanem et al. | |
| 2007/0239046 A1 | 10/2007 | Ghanem et al. | |
| 2007/0239047 A1 | 10/2007 | Ghanem et al. | |
| 2007/0239048 A1 | 10/2007 | Ghanem et al. | |
| 2007/0239049 A1 | 10/2007 | Ghanem et al. | |
| 2007/0239050 A1 | 10/2007 | Ghanem et al. | |
| 2007/0239051 A1 | 10/2007 | Ghanem et al. | |
| 2007/0239220 A1* | 10/2007 | Greenhut et al. | 607/32 |
| 2007/0270704 A1 | 11/2007 | Ghanem et al. | |
| 2008/0243025 A1 | 10/2008 | Holmstrom et al. | |
| 2008/0269813 A1 | 10/2008 | Greenhut et al. | |
| 2009/0093731 A1 | 4/2009 | Palreddy et al. | |

FOREIGN PATENT DOCUMENTS

| | | |
|---|---|---|
| EP | 0095727 | 12/1983 |
| EP | 0316616 | 5/1989 |
| EP | 0347353 | 12/1989 |
| EP | 0517494 | 12/1992 |
| EP | 0518599 | 12/1992 |
| EP | 0536873 | 4/1993 |
| EP | 0586858 | 3/1994 |
| EP | 0627237 | 12/1994 |
| EP | 0641573 | 3/1995 |
| EP | 0677301 | 10/1995 |
| EP | 0917887 | 5/1999 |
| EP | 0923130 | 6/1999 |
| EP | 1000634 | 5/2000 |
| EP | 1 745 741 A1 | 1/2007 |
| EP | 0813889 A2 | 5/2007 |
| WO | 9319809 | 10/1993 |
| WO | 9729802 | 8/1997 |
| WO | 9825349 | 6/1998 |
| WO | 9903534 | 1/1999 |
| WO | 9937362 | 7/1999 |
| WO | WO/99/48554 A1 | 9/1999 |
| WO | 9953991 | 10/1999 |
| WO | WO/2007/140209 A3 | 4/2000 |
| WO | 0041766 | 7/2000 |
| WO | 0050120 | 8/2000 |
| WO | 0143649 | 6/2001 |
| WO | 0156166 | 8/2001 |
| WO | 0222208 | 3/2002 |
| WO | 0224275 | 3/2002 |
| WO | 02068046 | 9/2002 |
| WO | 03/020367 A1 | 3/2003 |
| WO | 03018121 | 3/2003 |
| WO | WO/03/065613 A1 | 8/2003 |
| WO | 2004/091720 A2 | 10/2004 |
| WO | 2004 105871 A1 | 12/2004 |
| WO | 2007 089959 A1 | 8/2007 |
| WO | WO/2007/140207 A1 | 12/2007 |
| WO | WO/2007/140209 A2 | 12/2007 |
| WO | WO/2007/140214 A1 | 12/2007 |

OTHER PUBLICATIONS

Bardy, Gust H. et al., "Multicenter Experience with a Pectoral Unipolar Implantable Cardioverter-Defibrillator," JACC, Aug. 1996, vol. 28, No. 2, pp. 400-410.

Friedman, Richard A. et al., "Implantable Defibrillators in Children: From Whence to Shock," Journal of Cardiovascular Electrophysiology, vol. 12, No. 3, Mar. 2001, pp. 361-362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," Journal of Cardiovascular Electrophysiology, vol. 12, No. 3, Mar. 2001, pp. 356-360.

Higgins, Steven L. et al., "The First Year Experience with the Dual Chamber ICD," PACE, Jan. 2000, vol. 23, pp. 18-25.

Mirowski, M. et al., "Automatic Detection and Defibrillation of Lethal Arrhythmias-A New Concept," JAMA, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," IEEE, (1987) pp. 167-170.

Schuder, John C., "Completely Implanted Defibrillator," JAMA, vol. 214, No. 6, Nov. 9, 1970. p. 1123 (single sheet).

Schuder, John C. et al., "Experimental Ventricular Defibrillation with an Automatic and Completely Implanted System," Trans. Amer. Soc. Artif. Int. Organs, vol. XVI (1970) pp. 207-212.

Schuder, John C., "The Role of an Engineering Oriented Medical Research Group in Developing Improved Methods and Devices for Achieving Ventricular Defibrillation: The University of Missouri Experience," PACE, vol. 16, Jan. 1993, pp. 95-124.

Schuder, John C. et al., "Standby Implanted Defibrillators," Arch Intern. Med, vol. 127, Feb. 1971, p. 317 (single sheet).

Schuder, John C. et al., "Transthoracic Ventricular Defibrillation in the Dog with Truncated and Untruncated Exponential Stimuli," IEEE Transactions on Bio-Medical Engineering, vol. BME-18, No. 6, Nov. 1971, pp. 410-415.

Schwacke, H. et al., "Komplikationen mit Sonden bei 340 Patienten mit einem Implantierbaren Kardioverter/ Defibrillator," Z Kardiol (1999)vol. 88, No. 8, pp. 559-565.

Throne, Robert D., "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 6, Jun. 1991, pp. 561-570.

Tietze U. et al., "Halbleiter-Schaltungstechnik," © Springer-Verlag (Berlin, Germany), (1991) pp. 784-786.

Valenzuela, Terrence D. et al., "Outcomes of Rapid Defibrillation by Security Officers After Cardiac Arrest in Casinos," The New England Journal of Medicine, Oct. 26, 2000, vol. 343, No. 17, pp. 1206-1209.

Walters, R.A. et al., "Analog to Digital Conversion Techniques in Implantable Devices," Annual International Conference of the IEEE Engineering in Medicine and Biology Society, vol. 13 No. 4 (1991) p. 1674-1676.

Ge, Dingfei et al., "Cardiac Arrhythmia Classification Using Autoregressive Modeling," BioMedical Engineering OnLine, http://www.biomedical-engineering-online.com, Nov. 13, 2002, 12 pages.

U.S. Appl. No. 11/623,472 to Sanghera et al., filed Jan. 16, 2007.

U.S. Appl. No. 11/497,203 to O'Connor, filed Aug. 1, 2006.

U.S. Appl. No. 11/441,522 to Sanghera et al., filed May 26, 2006.

Burd et al.; "Utility of the Surface ECG Before VDD Pacemaker Implantation"; International Journal of Cardiology; vol. 117, No. 2, pp. 211-213; 2007.

Chrysostomakis, et al.; "Sensing Issues Related to the Clinical Use of Implantable Loop Recorders"; Europace; vol. 5, No. 2, pp. 143-148; 2003.

Chrysostomakis, et al.; "Implantable Loop Recorder Undersensing Mimicking Complete Heart Block"; Europace; vol. 4, No. 2, pp. 211-213; 2002.

U.S. Appl. No. 60/786,981, filed Mar. 29, 2006; Stadler, et al.

U.S. Appl. No. 60/632,000, filed Dec. 1, 2004; Gunderson.

U.S. Appl. No. 60/186,235; filed Mar. 1, 2000; Cao, et al.

* cited by examiner

SENSING VECTOR SELECTION IN A CARDIAC STIMULUS DEVICE WITH POSTURAL ASSESSMENT

CROSS-REFERENCE TO RELATED APPLICATIONS

This application is related to U.S. application Ser. No. 11/623,472, filed Jan. 16, 2007 and entitled SYSTEMS AND METHODS FOR SENSING VECTOR SELECTION IN AN IMPLANTABLE MEDICAL DEVICE USING A POLYNOMIAL APPROACH, the disclosure of which is incorporated herein by reference. This application is also related to U.S. application Ser. No. 11/441,522, filed May 26, 2006 and entitled SYSTEMS AND METHODS FOR SENSING VECTOR SELECTION IN AN IMPLANTABLE MEDICAL DEVICE; the disclosure of which is incorporated herein by reference.

FIELD

The present invention relates to the field of implantable medical devices. More particularly, the present invention relates to implantable devices that monitor and/or stimulate the heart.

BACKGROUND

Implantable cardiac monitoring and/or stimulus devices can provide various benefits to patients who receive them. Such devices are adapted to monitor cardiac activity of a patient while implanted and, if so equipped, to provide stimulus when necessary to assure adequate cardiac function. New and different methods are desired for configuring and performing cardiac signal assessment in such devices.

SUMMARY

The present invention, in an illustrative embodiment, includes an implantable medical device that includes sensing electrodes and circuitry that allow the device, when implanted in a patient, to sense electrical activity emanating from the patient's heart along a plurality of sensing vectors. In the illustrative embodiment, the implantable medical device is configured to select a primary or default sensing vector by observing cardiac signal characteristics along one or more of the plurality of sensing vectors. In an illustrative embodiment, observation of the cardiac signal characteristics includes initialization in terms of the body position or posture of the patient.

In another illustrative embodiment, a device as described above is included as a part of a system including an external programmer, wherein the programmer and implanted device are configured to communicate with one another. In this embodiment, the system is configured such that the patient may be directed to perform certain acts and/or assume selected postures/poses/body positions via the programmer, allowing the implanted device to observe the effects of changes of posture by the patient on captured cardiac signal. The implanted device (or the programmer, depending upon the particular configuration) may then select a primary or default sensing vector.

Another illustrative embodiment includes a method of selecting a vector for use in sensing cardiac events. In the illustrative method, sensing characteristics along several vectors may be considered with the patient in various body positions (for example, standing, sitting, and/or lying down). Using the captured sensing characteristics, a default or primary sensing vector may be selected. In an illustrative example, the method includes directing the patient to assume a set of postures/poses/body positions.

In addition to selecting a primary or default sensing vector, in some embodiments, a secondary vector is selected for various uses.

DETAILED DESCRIPTION

The following detailed description should be read with reference to the drawings. The drawings, which are not necessarily to scale, depict illustrative embodiments and are not intended to limit the scope of the invention.

The present invention is related to U.S. application Ser. No. 11/441,522, filed May 26, 2006 and entitled SYSTEMS AND METHODS FOR SENSING VECTOR SELECTION IN AN IMPLANTABLE MEDICAL DEVICE, the disclosure of which is incorporated herein by reference. In particular, the '522 application shows illustrative methods of analyzing cardiac signals captured along a given sensing vector. The methods shown therein are illustrative of analytical methods and "scoring" that may also be performed in association with the present invention.

Figure 1A:
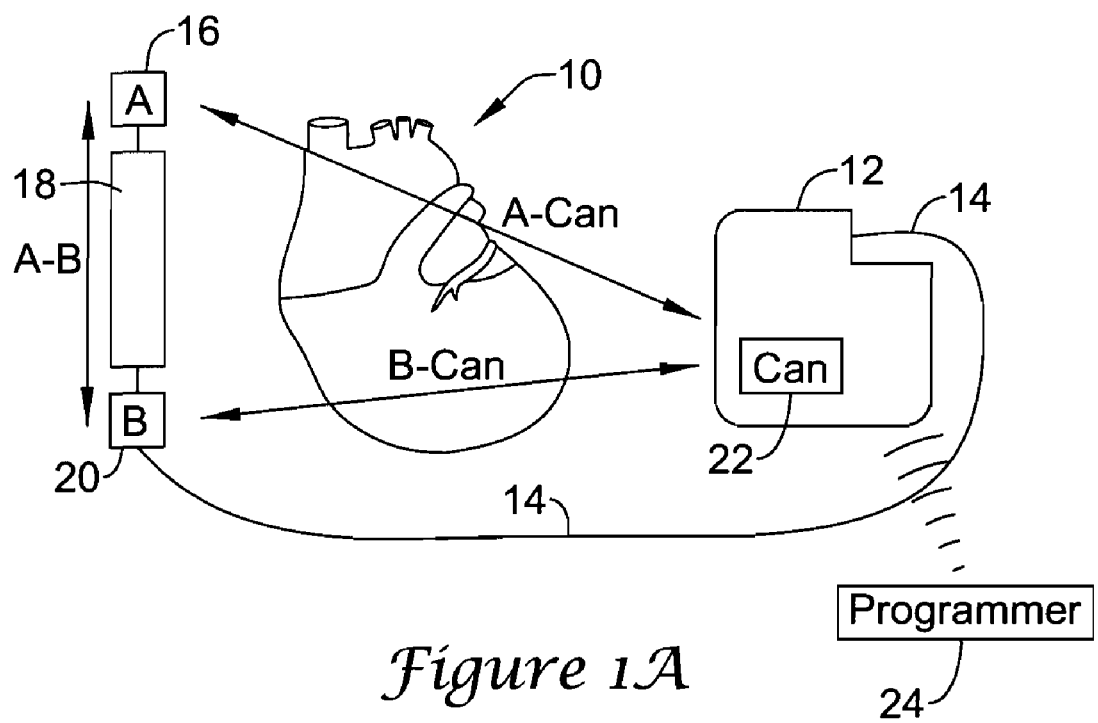
FIGS. 1A-1B illustrate subcutaneous and transvenous cardiac stimulators.
Figure 1B:
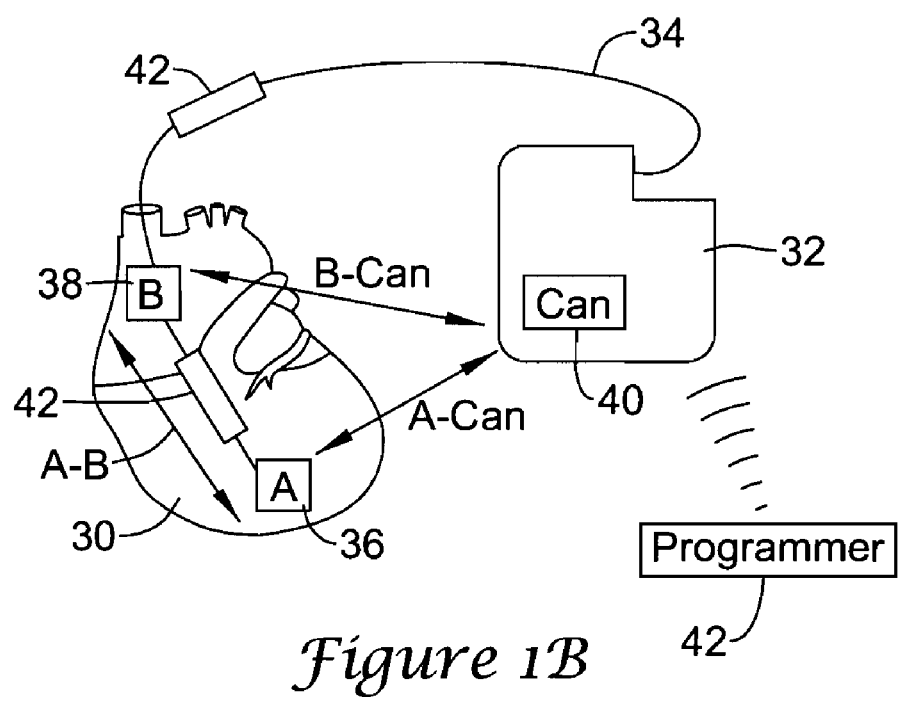

FIGS. 1A-1B, respectively, show subcutaneous and transvenous implanted cardiac stimulus systems relative to the heart. Referring to FIG. 1A, the patient's heart 10 is shown in relation to an implanted, subcutaneous cardiac stimulus system including a canister 12. A lead 14 is secured to the canister 12 and includes sensing electrode A 16, coil electrode 18, and sensing electrode B 20. A can electrode 22 is shown on the canister 12. Several vectors for sensing are therefore available including A-can, B-can, and A-B. It should be noted that the use of the coil electrode 18 as a sensing electrode is also possible. Illustrative subcutaneous systems are shown in U.S. Pat. Nos. 6,647,292 and 6,721,597, and the disclosures of these patents are incorporated herein by reference. Some embodiments include a unitary system having two or more electrodes on a housing as set forth in the '292 patent, rather than that which is shown in FIG. 1A. A unitary system including an additional lead may also be used. It should be understood that for any vector discussed herein, either of the two available polarities for each vector is possible and may be analyzed and/or selected, if desired.

Referring now to FIG. 1B, a transvenous system is shown relative to a patient's heart 30. The transvenous cardiac stimulus system includes a canister 32 connected to a lead 34. The lead 34 enters the patient's heart and includes electrodes A 36 and B 38. The illustrative example also includes coil electrodes 42, shown both internal and external to the heart 30.

The coil electrodes 42 may be used for sensing or stimulus delivery. In the illustrative example, electrode A 36 is located generally in the patient's ventricle, and electrode B 38 is located generally in the patient's atrium. The lead 34 may be anchored into the patient's myocardium. Again, a can electrode 40 is shown on the canister 32. With the transvenous system, plural sensing vectors may be defined as well.

In both FIGS. 1A and 1B, one or more sensing electrodes may also be used for stimulus delivery. Some embodiments of the present invention may be used in combination systems that may include sensing vectors defined between two subcutaneous electrodes, a subcutaneous electrode and a transvenous electrode, or two transvenous electrodes. For example, the present invention may be embodied in a hybrid system having electrodes for each of several transvenous, epicardial, and/or subcutaneous locations.

In the configurations of FIGS. 1A and 1B, there are multiple sensing vectors available. Detection of cardiac function along one of these sensing vectors allows the implanted cardiac stimulus system to determine whether treatment is indicated due to the detection and identification of a malignant condition such as, for example, a ventricular tachycardia. An implanting physician may perform vector selection by determining which of the captured vectors is best, for example by visual inspection of a graphical representation of captured signals. However, this requires an assessment of cardiac function along several vectors and may increase the time needed to perform implantation, and also increases the risk of human error. Further, the selection of a vector may require advanced or specialized training, as selection of a suitable vector among those available is not necessarily intuitive.

Robust sensing vector selection methods are desirable, as well as devices adapted to perform such methods. The present invention, in illustrative embodiments, provides such methods and uses various criteria for doing so. Some embodiments include implantable devices and programmers for implantable devices that are adapted to perform such methods.

The systems shown in FIGS. 1A-1B may include operational circuitry and power sources housed within the respective canisters. The power sources may be, for example, batteries or banks of batteries. The operational circuitry may be configured to include such controllers, microcontrollers, logic devices, memory, and the like, as selected, needed, or desired for performing the illustrative methods set forth herein. The operational circuitry may (although not necessarily) further include a charging sub-circuit and a power storage sub-circuit (for example, a bank of capacitors) for building up a stored voltage for cardiac stimulus taking the form of cardioversion and/or defibrillation. The operational circuitry may also be adapted to provide a pacing output. Each of cardioversion/defibrillation and pacing sub-circuitry and capacities may be incorporated into a single device. The methods discussed below may be embodied in hardware within the operational circuitry and/or as instruction sets for operating the operational circuitry and/or in the form of machine-readable media (optical, electrical, magnetic, etc.) embodying such instructions and instruction sets.

Each of the devices 12, 32 may further include such components as would be appropriate for communication (such as RF communication or inductive telemetry) with an external device such as a programmer. To this end, programmers 24 (FIG. 1A) and 42 (FIG. 1B) are also shown. For example, during an implantation procedure, once the implantable device 12, 32 and leads (if included) are placed, the programmer 24, 42 may be used to activate and/or direct and/or observe diagnostic or operational tests. After implantation, the programmer 24, 42 may be used to non-invasively determine the status and history of the implanted device. The programmer 24, 42 and the implanted device 12, 32 may be adapted for wireless communication allowing interrogation of the implanted device in any suitable manner for an implanted device system. The programmers 24, 42 in combination with the implanted devices 12, 32 may also allow annunciation of statistics, errors, history and potential problem(s) to the user or physician.

Figure 2:
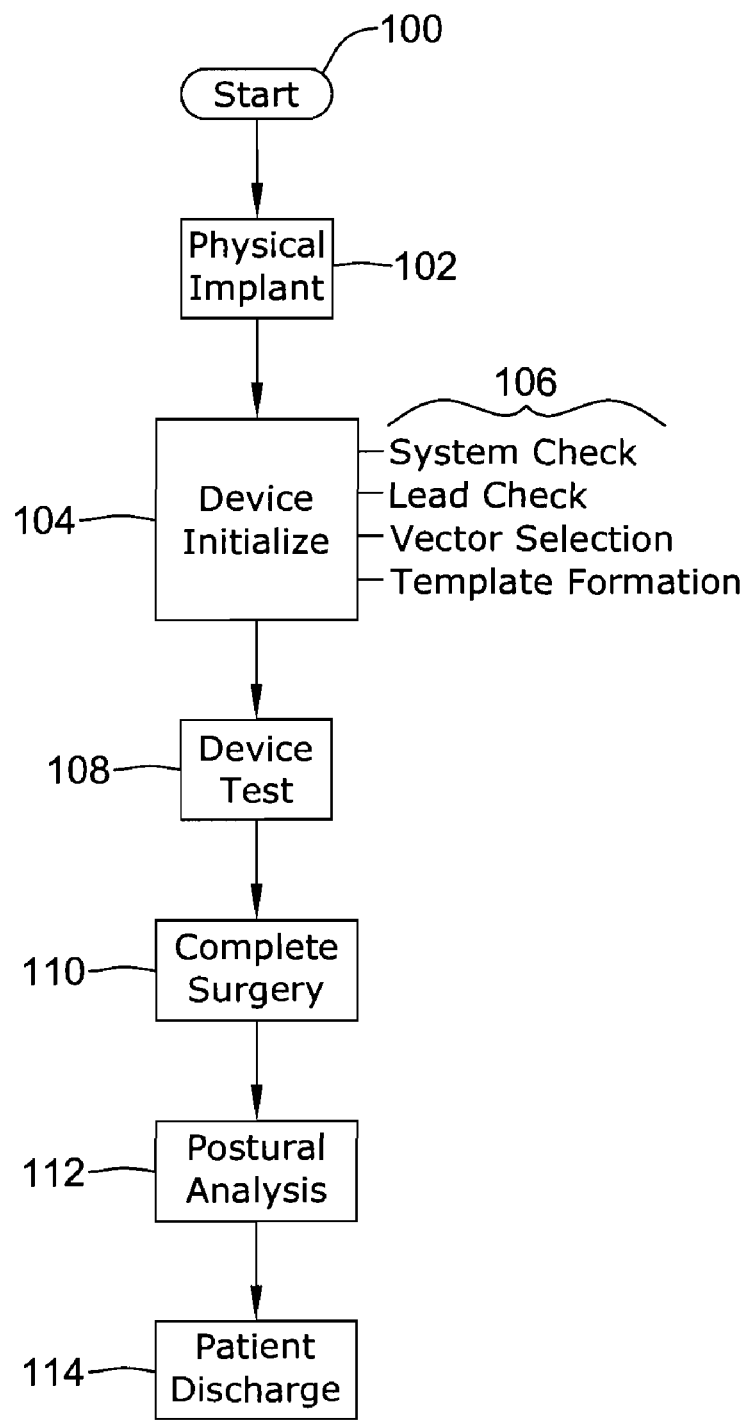
FIG. 2 is a block diagram illustrating steps in an illustrative implant procedure.

FIG. 2 is a block diagram illustrating steps in an illustrative implant procedure. From a start block 100, the first step is the physical implantation itself 102, which may include various surgical preparations as are known in the art, incision of the patient, and emplacement of a system, for example, a transvenous or subcutaneous system as shown above in FIGS. 1A-1B. Methods for physically implanting a transvenous device are well known. A subcutaneous device may be implanted, for example, as set forth in copending U.S. application Ser. No. 11/006,291, filed Dec. 6, 2004 and entitled APPARATUS AND METHOD FOR SUBCUTANEOUS ELECTRODE INSERTION, published as U.S. Pat. Pub. No. 2006/0122676; and/or copending U.S. application Ser. No. 11/497,203, filed Aug. 1, 2006 and entitled ELECTRODE INSERTION TOOLS, LEAD ASSEMBLIES, KITS AND METHODS FOR PLACEMENT OF CARDIAC DEVICE ELECTRODES, the disclosures of which are incorporated herein by reference.

With the system in place in the patient, the device is initialized, as indicated at 104. This may include various functions as indicated at 106, such as power-up of the device, system check, lead connection, detection and impedance checks. Initialization 104 may also include vector selection steps and template formation steps, allowing an initial set-up of the device while the patient is in the operating room. Illustrative methods of template formation are discussed in U.S. patent application Ser. No. 10/999,853, filed Nov. 29, 2004, now U.S. Pat. No. 7,376,458 and entitled METHOD FOR DEFINING SIGNAL TEMPLATES IN IMPLANTABLE CARDIAC DEVICES, the disclosure of which is incorporated herein by reference. Illustrative methods of vector selection are discussed in U.S. patent application Ser. No. 11/441,522, filed May 26, 2006, published as U.S. Patent Application Publication No. 2007-0276445 and entitled SYSTEMS AND METHODS FOR SENSING VECTOR SELECTION IN AN IMPLANTABLE MEDICAL DEVICE; U.S. patent application Ser. No. 10/901,258, filed Jul. 27, 2004, now U.S. Pat. No. 7,392,085 and entitled MULTIPLE ELECTRODE VECTORS ON A SUBCUTANEOUS ICD; and U.S. Pat. No. 6,988,003 entitled OPTIONAL USE OF A LEAD FOR A UNITARY SUBCUTANEOUS IMPLANTABLE CARDIOVERTER-DEFIBRILLATOR, the disclosures of which are incorporated herein by reference. The inclusion of each of functions 106 may vary depending upon the particular device.

After device initialization at 104, the device is tested as indicated at 108. For an implantable cardioverter defibrillator (ICD), for example, fibrillation may be induced in the patient in order to determine whether the ICD accurately senses the fibrillation and successfully delivers therapy that returns the patient to normal cardiac rhythm. If testing is unsuccessful, or if the device does not initialize, the system may be explanted. If, instead, the initialization at 104 is completed successfully and the system passes device testing at 108, then the surgical portion of the implantation is completed, as shown at 110, with appropriate methods including closing incisions made during implantation, etc.

In the illustrative method, postural analysis 112 follows completion of the surgical portion of the implantation method. During postural analysis 112, after the patient has had the device inserted and activated, and, possibly, after the patient has had time to recuperate somewhat, the operation of the implanted device is observed and may be modified. In particular, the patient may be asked to assume a series of positions, for example, sitting down and then standing up, while the implanted device gathers data to determine which of its available sensing vectors is best suited to permanent operation. In one illustrative example, the patient is led through a series of body positions such that the device may determine a single sensing vector for use as a primary or default sensing vector all the time, such that changes in sensing operation do not have to occur whenever the patient changes posture or body position.

In another illustrative example, an optimal or best vector is determined for each of the several body positions, and body position is monitored during operation such that the implanted device may select the optimal vector for a patient's current body position. Body position may be monitored, for example, by the provision of physical sensors that detect body position by reference to gravity, to movements, or the like. Transthoracic impedance can be used to provide a measure of patient body position, for example. An activity sensor may be used to infer whether the patient is standing versus lying down. Alternatively, body position may be monitored by observation of captured electric signals. For example, during postural analysis 112, the system may be configured to identify signal markers to differentiate cardiac signals captured while the patient is in each of several body positions and, thereafter, to identify the patient's body position by observation of the patient's cardiac signals.

Once postural analysis 112 is complete, the patient may then be discharged 114, as the implantation procedure and process is then complete. Following discharge 114, the patient may be requested to return for further diagnostics, for example, initialization may be updated (such as functions 106) and the postural analysis 112 may be later repeated. This may be done, for example, as the patient's physiology changes due to reaction to the implantation itself, with changes in patient medication, and/or as the patient ages.

Figure 3:
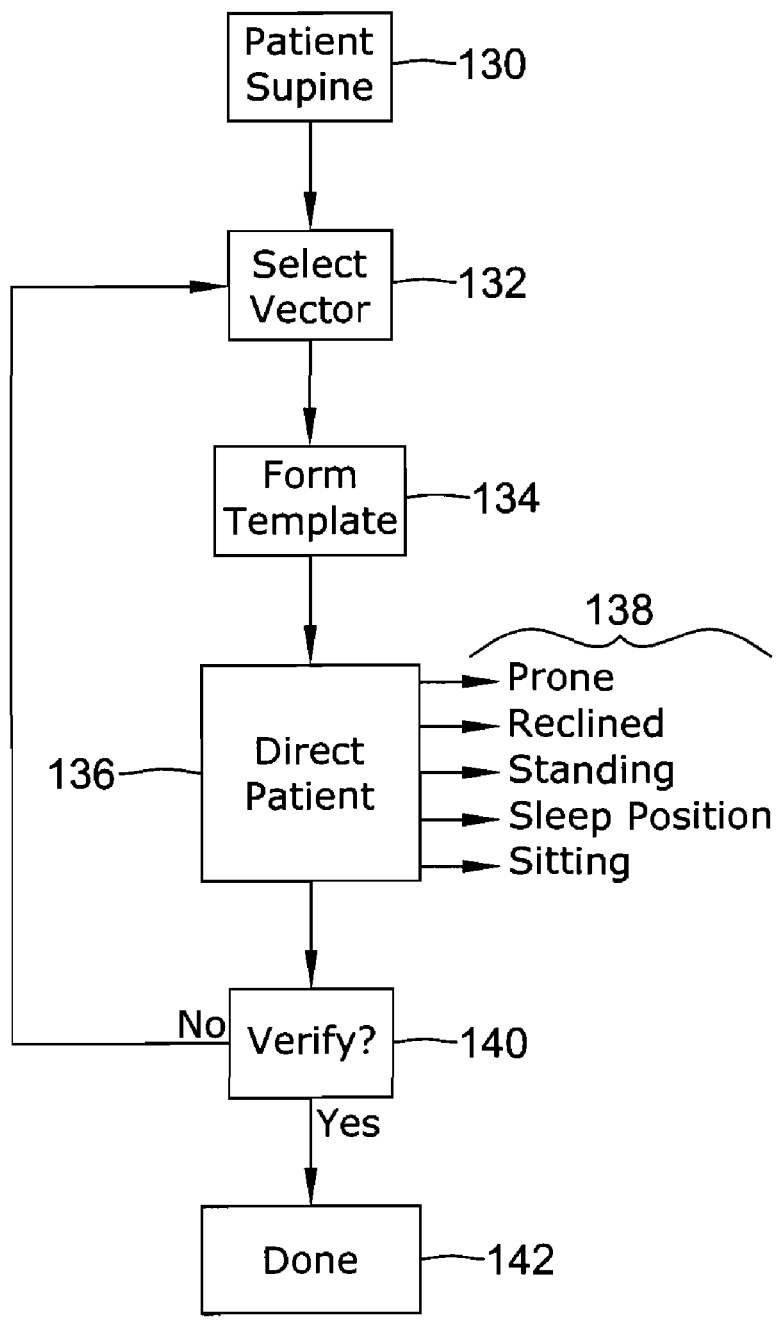
FIGS. 3-5 show illustrative methods of postural assessment in an implanted medical device.
Figure 4:
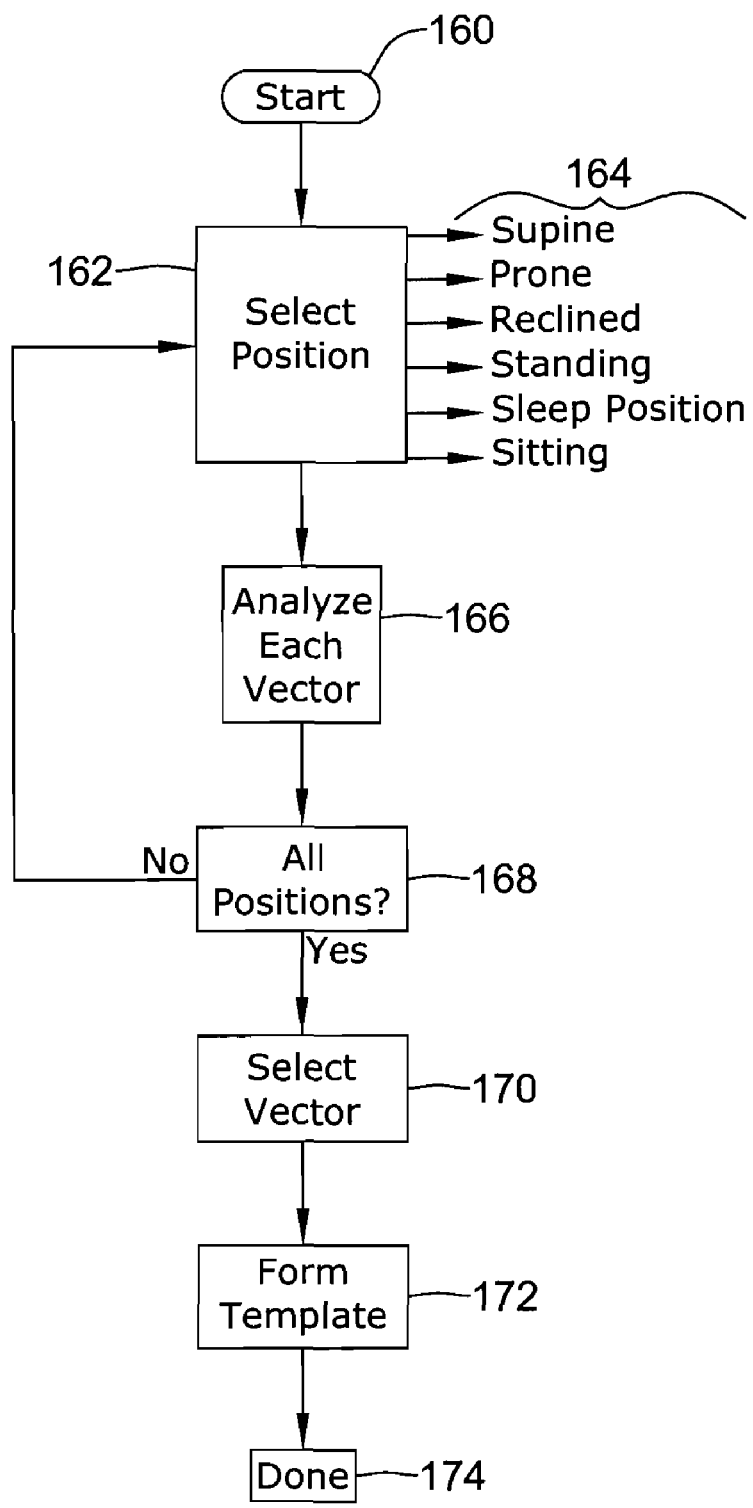
Figure 5:
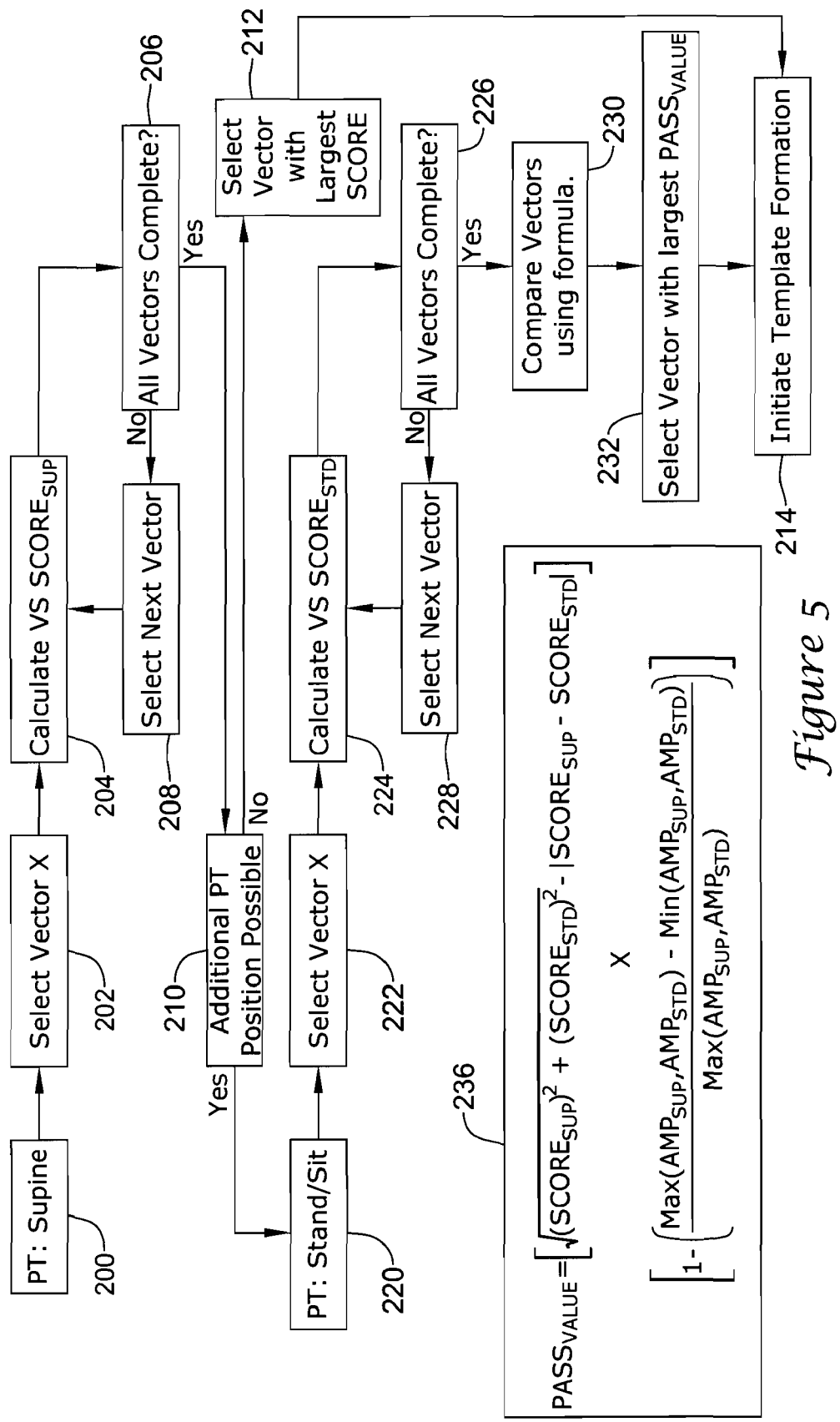

FIGS. 3-5 show illustrative methods of postural assessment in an implanted medical device. FIG. 3 illustrates a confirmation approach to postural assessment, in which a vector is identified on the basis of its characteristics while the patient is in a given body position, and the identified vector is then checked to confirm that it is usable regardless of the body position of the patient. The method begins at block 130, with the patient in a given body position, in this instance, supine. In other embodiments, the patient may begin in a different body position, such as prone, reclined, standing, or in whatever position the patient prefers to sleep in, for example.

With the patient in the given position, a vector is selected, as shown at 132. A vector may be selected at 132, for example, on the basis of the signal-to-noise ratio (SNR) of cardiac signals captured along that vector. Other metrics for selecting a vector at 132 may include signal amplitude, noise amplitude, etc. In an illustrative embodiment, a combination of SNR and signal amplitude are taken into consideration. For example, a formula using both SNR and amplitude may be used. Some illustrative examples of such analysis are shown in copending U.S. application Ser. No. 11/441,522, filed May 26, 2006 and entitled SYSTEMS AND METHODS FOR SENSING VECTOR SELECTION IN AN IMPLANTABLE MEDICAL DEVICE.

In another illustrative embodiment, a default vector is assumed, rather than selected on the basis of any metric. For example, if a particular system and implantation has a vector that works for most patients, then that vector may be selected first to start analysis. In another example, there may be a preferred vector, such as where there are two sensing-only electrodes and one or more sensing/shocking electrodes. Due to possible physical changes at the electrode/tissue interface for the sensing/shocking electrodes when stimulus is delivered, the vector between the two sensing-only electrodes may be "preferred". Thus, in starting the method, the "preferred" vector may be selected at step 132.

With the vector selected at 132, a template for analysis of cardiac signals may optionally be formed, as shown at 134. This optional step of the method of FIG. 3 may include capturing a set of signals with the selected vector, identifying likely cardiac events in the set of signals, and forming windows of captured signals around fiducial points likely to correspond to cardiac events.

An illustrative example of template formation may be as follows. First, the signal captured along the selected vector may be compared to a threshold and, when the threshold is exceeded, a cardiac event is assumed to be likely. A peak value in a set of samples following the threshold crossing (for example, the next 40 sequential samples, captured at 256 Hz) is identified as a fiducial point, and a window of samples around the fiducial point is calculated. This initial capture is presumed to be a cardiac event. Several additional "events" are subsequently captured in association with later threshold crossings, with the fiducial point and/or window being selected in a manner corresponding to that of the original identified "event".

The captured events are then compared to one another, for example, using correlation waveform analysis, or alternatively, another metric such as QRS width, which may be identified as a duration in which the signal remains above a minimum threshold. If the set of events is sufficiently similar, then a template is formed by selecting a representative event or by averaging a set of events. In some embodiments, the template may be dynamically updated by averaging in later-captured events. Additional examples of template formation may also be found in U.S. patent application Ser. No. 10/999,853, filed Nov. 29, 2004, now U.S. Pat. No. 7,376,458 and entitled METHOD FOR DEFINING SIGNAL TEMPLATES IN IMPLANTABLE CARDIAC DEVICES. In some embodiments, template formation may fail where similarity among sets of captured events does not occur. For example, a time-out may be used, and, if after a period of time (60-180 seconds, for example), a template cannot be formed using similarity analysis, the vector under consideration may be identified as poorly suited to detection.

Next, the patient is directed to change body positions, as indicated at 136. One or more additional positions beyond the original position may be used. For example, if the patient is supine, as indicated at 130, the patient may be asked to move to a prone position, to sit up, and/or to stand. The positions listed at 138 are merely illustrative, and no set number of such positions is necessary. In an illustrative embodiment, it is determined what positions the patient tends to rest in, for example, reclined, and/or the patient's sleep position, such as on the patient's side, in order that the posture assessment considers those positions the patient is in the most. For each position the patient is asked to assume, the implanted device analyzes the selected vector to determine whether the selected vector will function adequately for cardiac event detection and analysis. In an illustrative example, if the selected vector fails to function adequately in any position, the method skips any remaining body positions and advances to step 140. Otherwise, the selected vector is analyzed at each of at least two positions.

In an illustrative example, the selected vector is analyzed in each of the positions by considering one or more of SNR, signal amplitude, and/or noise amplitude. For example, the SNR and signal amplitude may be considered by the use of a formula, as further explained below.

The method then goes to step 140, where it is determined whether the selected vector has been verified or confirmed as a "good" sensing vector. If so, the method ends at 142. If the selected vector is not verified or confirmed, the method returns to step 132 and selects a different vector, with the patient being asked to again assume the first body position upon return to step 132 and, thereafter, to move through additional body positions as directed at step 136. In this method, a vector is first selected and then tested as the patient changes body positions.

FIG. 4 illustrates a deterministic approach, as contrasted to the confirmation approach of FIG. 3. In FIG. 4, for example, the patient assumes a given body position and holds that position until data is gathered for each of the available vectors. The method of FIG. 4 begins with start block 160. The patient is asked to select a body position, as indicated at 162. Illustrative positions are listed at 164; in an example, the patient is asked to lay supine and is later asked to sit and/or stand. Each vector is then analyzed while the patient remains in the selected body position, as shown at 166. After data is captured for each vector during step 166, it is determined if all positions have been tested, as indicated at 168. If not, the method returns to step 162, where a different body position is selected and the patient is asked to assume a different body position. Once each desired body position is tested, the method exits the loop from 168, and a vector is selected as indicated at 170. Once a vector is identified on the basis of the data captured in the loop of 162-166-168, the method may perform template formation as indicated at 172. In some embodiments, if template formation 172 fails, the method may return to step 170 and select a different vector. The method then ends, as indicated at 174.

In an alternative embodiment, first and second vectors are identified, with the second vector being a back-up vector for use either because the first, primary or default vector becomes unavailable or, alternatively, for use if the first vector provides ambiguous indications of whether the patient is experiencing an arrhythmia.

In some embodiments, a single vector is identified for use while the patient is in any body position. In other embodiments, several templates may be formed for the patient. For example, analysis of data captured while the patient is in a supine position may indicate a different "best" vector than that captured while the patient is an upright position. Two templates could then be formed, without regard for whether the first and second templates are formed using the same vector, where each template includes information for its sensing vector configuration.

Illustratively, the first template could use sensing vector A-Can (see FIG. 1A) and could be defined at the time of postural assessment while the patient is supine, and the second template could use vector A-B (see FIG. 1A) and could be defined at the time of postural assessment while the patient is sitting upright. Then, during analysis, the primary template at any given time could be whichever indicates ordinary cardiac function. If neither template indicates ordinary cardiac function, it may be presumed that an arrhythmia is occurring, and a stimulus may be delivered. This may be performed as part of a Boolean approach to finding arrhythmic activity:

---
IF Analysis(A) fails
AND IF Analysis(B) fails
THEN Event indicates Malignant Rhythm

---

This tiered analysis may prevent misdiagnosis of the cardiac rhythm due to a change of the patient's body position.

In another illustrative example, the primary and secondary templates may be "switched" one for the other in response to an output from a body position sensor. For example, if the primary template is associated with a first body position and the secondary template is associated with a second body position, an output of a body position sensor may be monitored, and the templates switched depending upon the body position indicated by the body position sensor.

Additionally, switching between the templates may be achieved without needing the use of a dedicated position sensor. In an illustrative example, only the Analysis(A) is performed in a morphology-based analysis system until a first threshold of abnormality is met. For example, if an X out of Y counter is used, the Analysis(A) may be used by itself until a first X out of Y threshold is met. In an illustrative example, if 18/24 events is the threshold for a determination that a malignant cardiac rhythm is occurring, then an 8/24 threshold may be used to activate Analysis(B). If 2-3 events occur before Analysis(B) begins functioning, then a smooth transition may occur if the patient has changed positions since, by the time the 18/24 counter fills for Analysis(A), 8 or more events will have been detected using Analysis(B). In an illustrative example, if 4/8 of the events using Analysis(B) are found to meet template comparison parameters, the system may switch to Analysis(B), using a different template and/or vector than Analysis(A) for primary analysis. In some illustrative embodiments that use both primary and secondary templates, stimulus delivery (or preparation for stimulus delivery) may be delayed until it is determined that the analysis with each template indicates a malignant cardiac rhythm.

The method of FIG. 4 calls for more data to be gathered than the method of FIG. 3, regardless of whether one vector is superior or not. Therefore, this method may be slower in some instances than that of FIG. 3. However, with the method of FIG. 3, the patient may be asked to perform and repeat several movements during postural assessment. If a device is implanted in a patient who is relatively weak, for example, due to advanced congestive heart failure, repeated movements may be undesirable. Illustrative examples may be configured to perform either method. In another illustrative example, the devices (the implanted medical device and/or the programmer) in the system are equipped to perform either method, with the programmer allowing a physician to select one method or the other.

FIG. 5 illustrates a detailed method for an illustrative embodiment. As indicated at 200, the method begins with the patient (PT) supine. Step 200 may be a directive given from the programmer to a physician to have the patient assume a supine position, or it may be given directly to the patient from the programmer itself. With this position verified (for example, the programmer may request an input indicating that the patient is in the requested position), a first vector is selected, as indicated at 202.

A VS SCORE$_{SUP}$ is then calculated, as indicated at 204. The VS SCORE$_{SUP}$ may be a "score" calculated to indicate the quality of the sensing vector. As discussed above, this may include consideration of signal amplitude, SNR, etc. Calculation of a SCORE may make use of a formula, a look-up table, or any suitable method for placing a metric on the quality of a sensing vector. Illustrative methods are shown in copending U.S. application Ser. No. 11/441,522, filed May 26, 2006 and entitled SYSTEMS AND METHODS FOR SENSING VECTOR SELECTION IN AN IMPLANTABLE MEDICAL DEVICE.

After the score is calculated at 204, it is determined whether all vectors have been analyzed, as indicated at 206. If not, a different vector is selected, as shown at 208, and the method calculates another VS $SCORE_{SUP}$ at 204. If all the vectors have been considered at step 206, the method continues to block 210.

At block 210, the programmer or the implantable device, depending on the system configuration, determines whether additional patient positions are possible. If not, the method continues to step 212, where the vector having the largest SCORE from the initial analysis is selected for use in analysis, and template formation is initiated, as indicated at 214. This opt-out step 210 may be provided to accommodate a patient who is not capable of changing body positions due to physical limitations or to accommodate use during implant procedures.

If, at step 210, one or more additional patient positions are possible, the method continues to step 220. At step 220, the programmer requests that the patient adopt a different position, for example, standing or sitting. The method then performs similar steps to those performed with the first body position. A vector is selected at 222, a score, VS $SCORE_{STD}$, is calculated at 224, and it is determined whether each vector has been considered at 226. If not, as indicated at 228, the method returns to 224 with a different vector selected. Once all vectors are completed, the vectors are compared, as indicated at 230. In an illustrative embodiment, the formula shown at 236 is used to calculate a $PASS_{Value}$ for each vector.

Figure 6A:
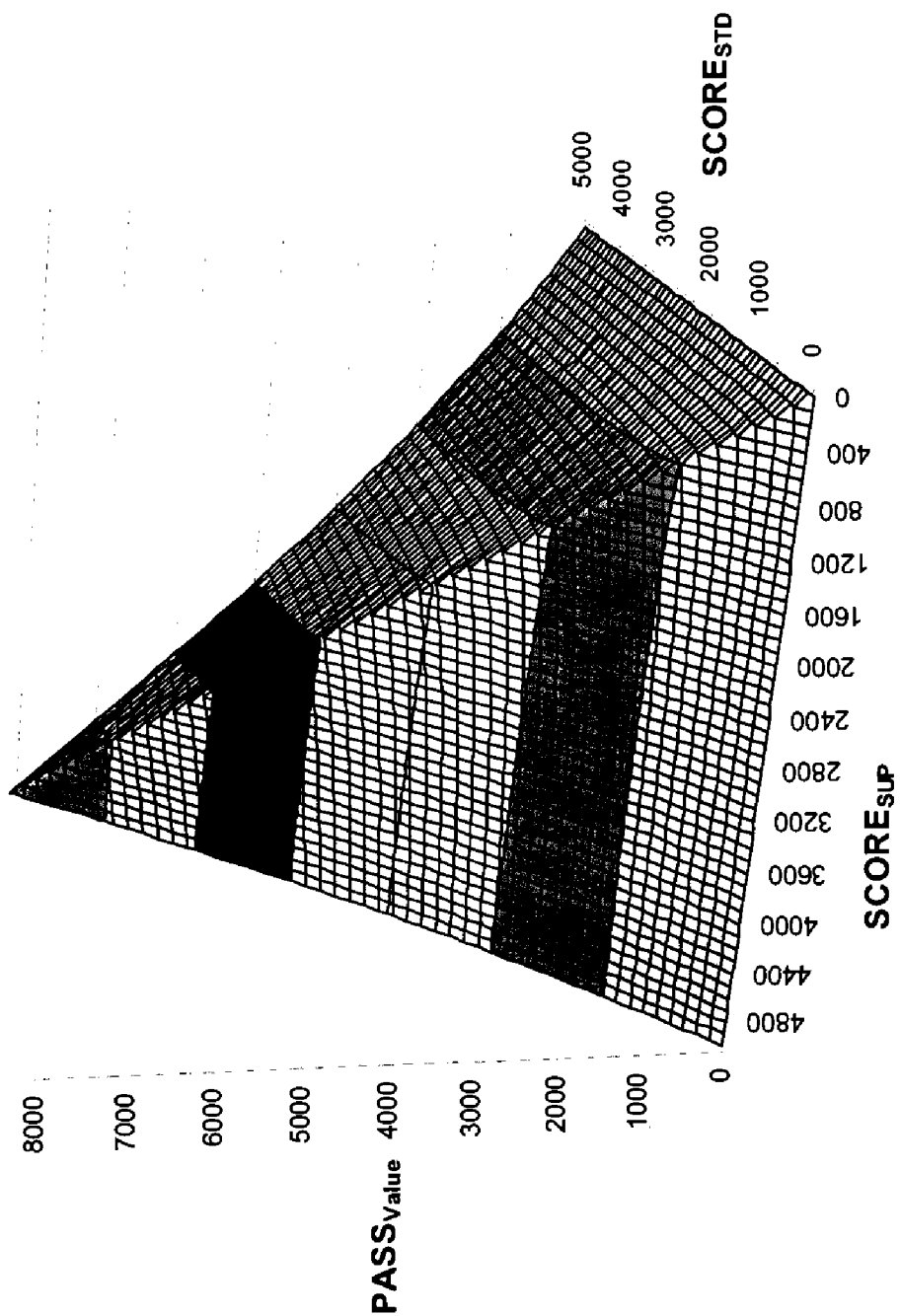
FIGS. 6A-6B are graphs of variable relationships in an illustrative method of analyzing sensing vectors during postural assessment.
Figure 6B:
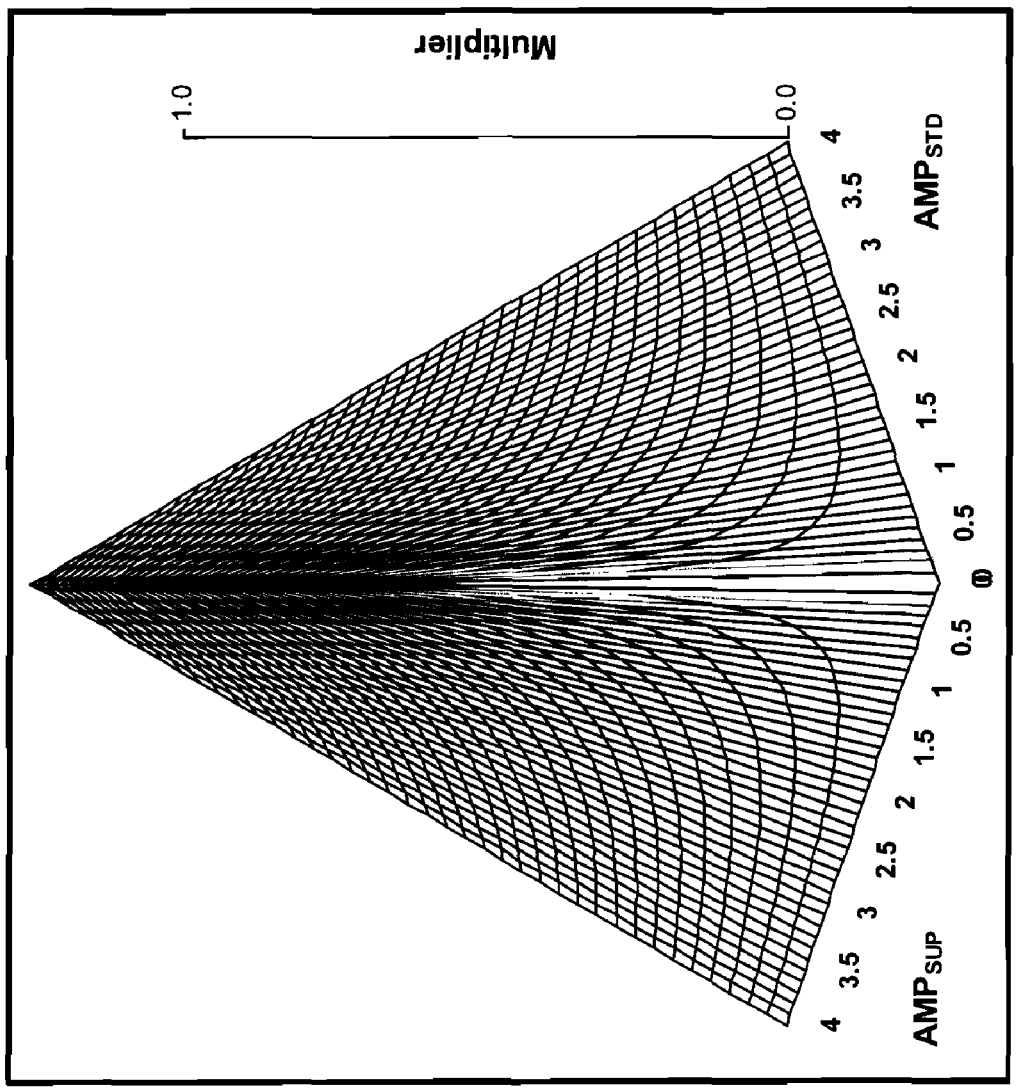

Formula 236 includes two major terms. FIGS. 6A-6B are graphs of variable relationships in an illustrative method of analyzing sensing vectors during postural assessment, with FIG. 6A illustrating the first term:

$$\sqrt{(SCORE_{SUP})^2 + (SCORE_{STD})^2} - |SCORE_{SUP} - SCORE_{STD}|$$

The result of this first term increases with the amplitude of each SCORE, and is greatest when the amplitudes of the SCOREs are similar.

FIG. 6B illustrates relationships for the second term:

$$1 - \left(\frac{Max(AMP_{SUP}, AMP_{STD}) - Min(AMP_{SUP}, AMP_{STD})}{Max(AMP_{SUP}, AMP_{STD})}\right)$$

When the signal amplitudes are closest to one another, the value of this term approaches 1, while it approaches zero if the maximum signal amplitude of the sensing vector when the patient is in one body position is significantly different from the maximum signal amplitude of the sensing vector when the patient is in the other body position.

In short, illustrative formula 236 takes into account the size and similarities of the SCOREs, i.e., whether the vector quality is high and the strength of the signal along a given vector is high in the first term, and whether the vector provides relatively consistent output, particularly in terms of signal amplitude, without regard for the body position of the patient.

One reason for the inclusion of the second term is that, in the illustrative embodiment, the event detection system of the implantable device includes an amplifying input having two dynamic ranges, one which is larger and one which is smaller. With such a system, it may be better, in some embodiments, to select a vector that captures signal that makes relatively full use of one of the dynamic ranges in each of the patient body positions.

Figure 7A:
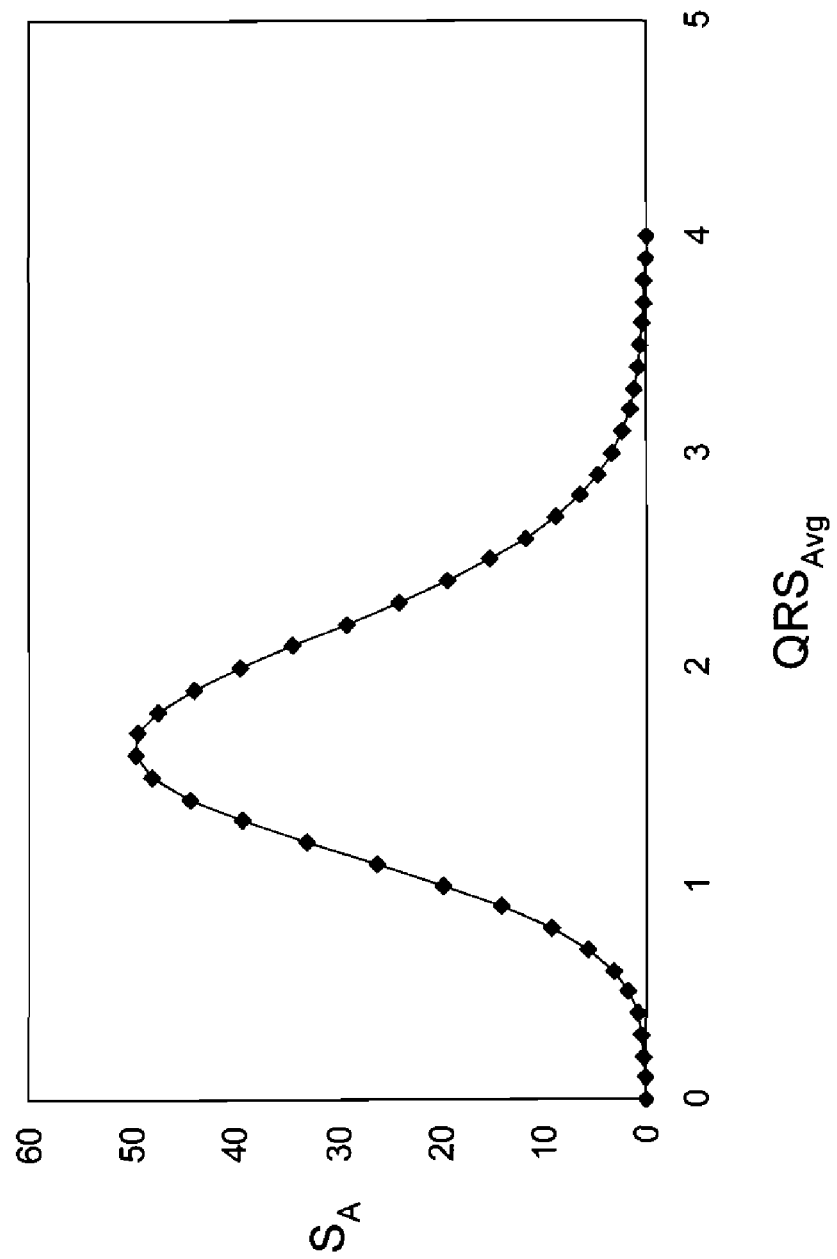
FIGS. 7A-7C are graphs of variable relationships in illustrative signal analysis methods.

For example, given dynamic ranges of 0-2.0 mV and 0-4.0 mV, analysis may be easier and more reliable with a first vector in which peak voltages are 0.75 mV for both body positions, rather than a second vector in which peak voltages are 0.75 mV for one body position and 2.5 mV for a second body position, as the latter vector would call for lower amplification to accommodate the second body position but would use the dynamic range poorly when the patient is in the first body position. For example, FIG. 7C illustrates a SCORE calculation in which the amplitude affects the output SCORE in a manner having first and second peaks, with a trough therebetween. While having both terms account for dynamic range is part of some illustrative embodiments, other illustrative embodiments may instead use the formula of FIG. 7A for score calculation, as further explained below.

The illustrative formula 236 presumes a SCORE value is generated in some manner. Some illustrative embodiments use the following approach:

$$SCORE = S_A \times S_R$$

Where, for example, $S_A$ and $S_R$ may be calculated using one of several approaches. In one such embodiment, the following formula is used:

$$S_A = GAIN * \frac{\exp(N1 * [\ln(N2 * QRS_{Avg} - N3)]^2)}{D1 * QRS_{Avg} - D2}$$

$$GAIN = 64.0 \quad N1 = -34.7222$$
$$Where: \quad N2 = 0.2326 \quad N3 = -0.6047$$
$$D1 = 0.3008 \quad D2 = -0.7821$$

It should be noted that the limits for $QRS_{Avg}$, in this illustrative embodiment, are $0 < QRS_{Avg} < 4.0$. A graph illustrating the relationship between $S_A$ and $QRS_{Avg}$ is shown in FIG. 7A.

The illustrative Scoring method further includes calculating a value $S_R$ as:

$$S_R = C_R * (SNR)^2$$

Figure 7B:
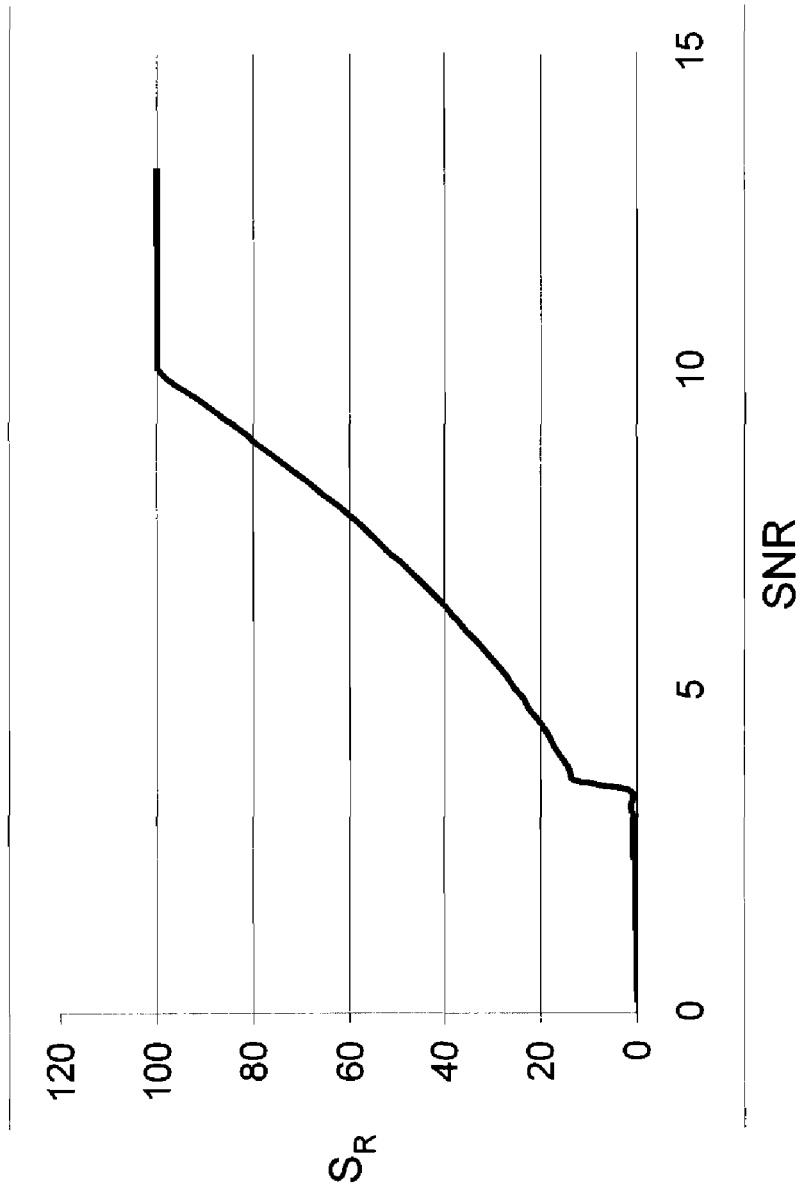
Figure 7C:
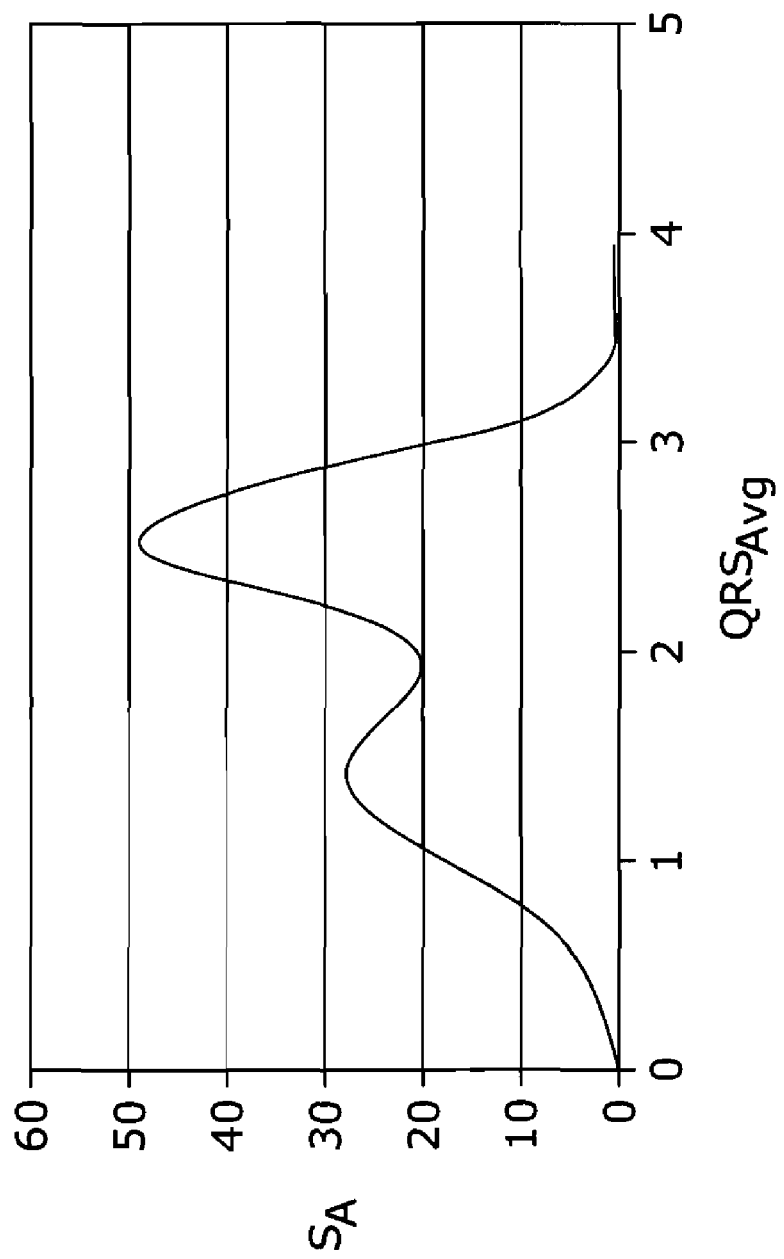

Where: if $SNR \leq 3.5$, $C_R = 0.1$;
if $3.5 < SNR \leq 10$, $C_R = 1$; and
if $SNR > 10$, $S_R = 100$ A graph illustrating the relationship between $S_R$ and the SNR is shown in FIG. 7B.

In another embodiment, $S_A$ and $S_R$ may be calculated from the following look-up table:

LOOKUP TABLE

| $S_A$ | $QRS_{Avg}$ (mV) | $S_R$ | SNR |
|---|---|---|---|
| 0.5 | ≤0.5 | 0.5 | ≤3 |
| 5 | 0.5-0.65 | 1 | 3-3.5 |
| 10 | 0.65-0.8 | 25 | 3.5-4 |
| 18 | 0.8-1.0 | 50 | 4-5 |
| 30 | 1.0-1.7 | 75 | 5-7.5 |
| 20 | 1.7-2.0 | 100 | >7.5 |
| 40 | 2.0-3.0 | | |
| 15 | 3.0-3.5 | | |
| 0.5 | 3.5-4.0 | | |

It can be seen that the output scores using the lookup table would include a trough in the range of 1.7 mV<$QRS_{Avg}$<2.0 mV, in accordance with an embodiment adapted for multiple dynamic ranges.

In yet another embodiment, $S_A$ and $S_R$ are calculated using another polynomial formula, for example:

$$S_R = C_R*(SNR)^2$$

where: if SNR≦3.5, $C_R$=0.1;
if 3.5<SNR≦10, $C_R$=1; and
if SNR>10, $S_R$=100

It can be seen that $S_R$ is calculated the same here as in the first calculation method shown above, and a graph showing the relationship is shown in FIG. 7B. In this illustrative example, $S_A$ may be calculated using the following:

$$S_A = \{C_1*(QRS_{Avg})^6 + C_2*(QRS_{Avg})^5 + C_3*(QRS_{Avg})^4 + C_4*(QRS_{Avg})^3 + C_5*(QRS_{Avg})^2 + C_6*(QRS_{Avg}) + C_7\}$$

where, if $QRS_{Avg}$≦2.0,
$C_1$=22.5718 $C_2$=−105.9666 $C_3$=160.2345
$C_4$=−88.9262 $C_5$=29.6019 $C_6$=−1.2859
$C_7$=0.0087
and, if $QRS_{Avg}$>2.0,
$C_1$=56.5544 $C_2$=−1069.9959 $C_3$=8310.0056
$C_4$=−33849.9682 $C_5$=76139.7271 $C_6$=−89551.3405
$C_7$=43035.7880

A graph illustrating the relationship between $S_A$ and $QRS_{AVG}$ is shown in FIG. 7C. Both the lookup table and this third method using a $6^{th}$ order polynomial take into account a system having first and second dynamic ranges by providing a dip in the SCOREs corresponding to input signals that would border between the two dynamic ranges.

These methods of calculating SCOREs are merely illustrative, and those of skill in the art will understand that the values and calculations involved will vary depending upon the positioning of the system, the electronics and electrodes used, power level(s), and, potentially, other variables.

It is sufficient for the present invention that an analysis of a sensing vector is performed with the patient in two or more body positions, if two positions are possible, and that this analysis provides a result that indicates whether or not the vector is useful/usable. For some embodiments, the analysis may further provide results for several vectors such that the vectors may be compared to one another. For example, in the method of FIG. 3, a Boolean output of Yes/No may be a result of vector analysis such that, if a vector is initially selected and is functional, a Yes output results. For the method embodiments of FIGS. 4-5, however, an output of vector analysis that allows comparative analysis is illustrated, as it allows the vectors to be compared to one another at the end of analysis. In alternative embodiments, a method as in FIGS. 4-5 returns Boolean results, with the available vectors prioritized such that the highest priority vector returning a functional result (Yes output, for example) is selected.

Referring again to FIG. 5, after comparison of the vectors at 230, the vector with the largest $PASS_{Value}$ is selected as the default or primary sensing vector, as indicated at 232. Template formation may then be initiated, as indicated at 214, and the device may move on to ordinary function. If desired, a secondary sensing vector may also be identified in step 232. A secondary sensing vector may be used, for example, for any of the reasons set forth above, including to resolve ambiguities, to provide a Boolean check of cardiac function, or to provide a second vector to use when the patient changes body position.

In a more general embodiment making use of similar relationships, the first formula could be of the form:

$$\frac{\sqrt{\sum_{i=1}^{i=n}(SCORE_n)^2}}{[\text{Max}(SCORE_1 \ldots SCORE_n) - \text{Min}(SCORE_1 \ldots SCORE_n)]}$$

where n is the number of body positions tested, and $SCORE_i$ is the score for the vector while the patient is in the $i^{th}$ body position. The amplitude factor may be analogous to the above amplitude factor. An additional factor which may be included takes the form:

$$\frac{\text{Min}(SCORE_1 \ldots SCORE_n)}{\text{Max}(SCORE_1 \ldots SCORE_n)}$$

This term would further emphasize a minimum score value, for example, when using three body positions in the postural assessment, if a very low score is achieved in any of the positions, the vector under consideration may be poorly suited to detection regardless of high SCOREs in the other positions, and this factor would reduce the output PASS value.

FIGS. 8A-8E are graphical representations of display outputs of a programmer during an illustrative method of postural assessment. In the illustrative embodiment, the programmer includes a touch screen; in other embodiments, the programmer may include buttons, a keypad or other controls, and may take any suitable form.

Figure 8A:
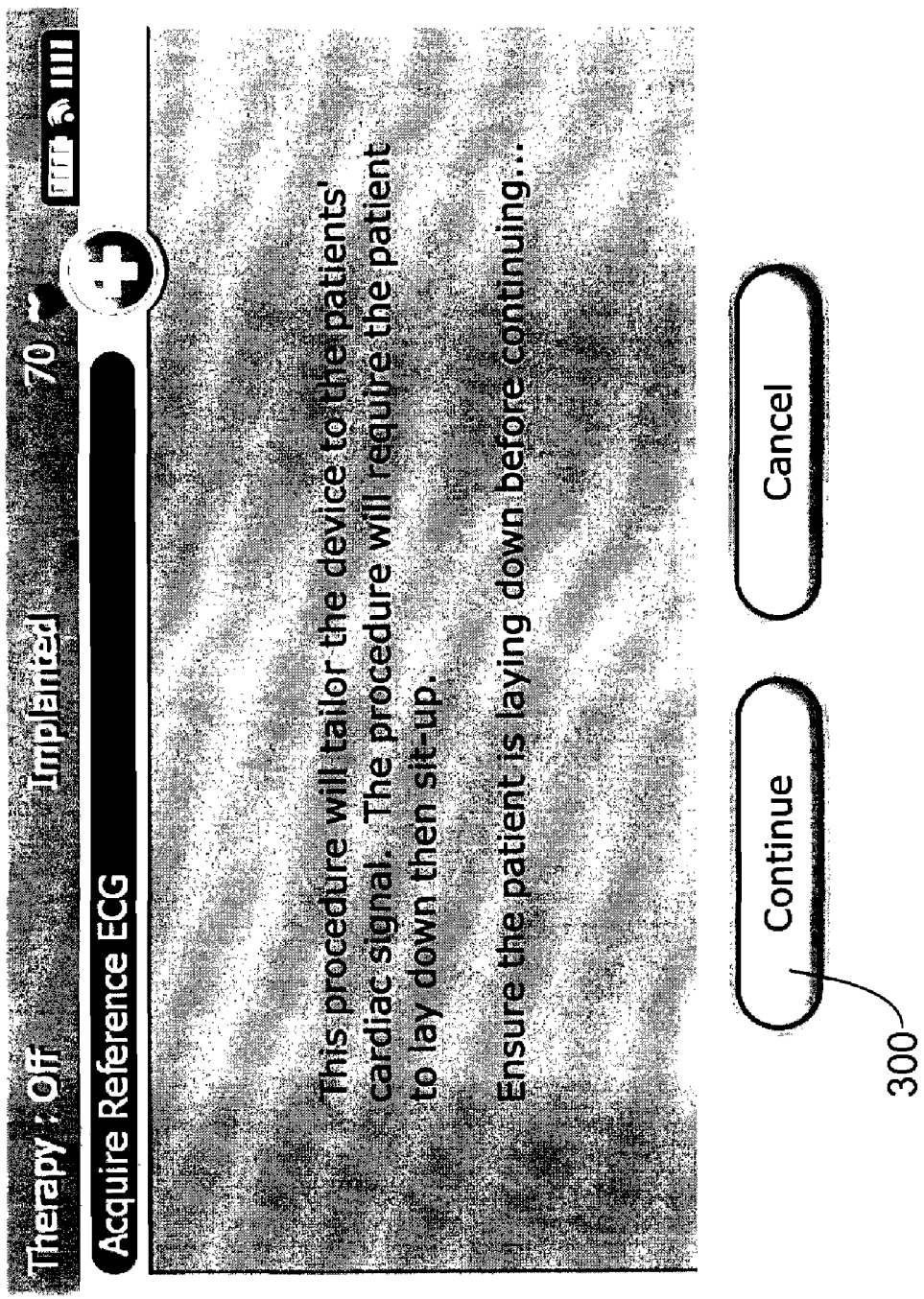
FIGS. 8A-8E are graphical representations of display outputs of a programmer during an illustrative method of postural assessment.

FIG. 8A shows a first screen shot. The programmer indicates to the physician that the postural assessment procedure is to start. The physician is asked to ensure that the patient is laying down (a first body position) and then to touch the "continue" icon 300 on the screen. Across the top of the programmer screen, status is indicated for the implanted device. In particular, during these steps, therapy for the device may (optionally) be turned off. The device status as "implanted" is indicated, as is the patient's heart rate. In some embodiments, the programmer may refuse to perform postural assessment if the patient's heart rate is not in a predetermined range, for example, between 50 and 120 bpm.

Figure 8B:
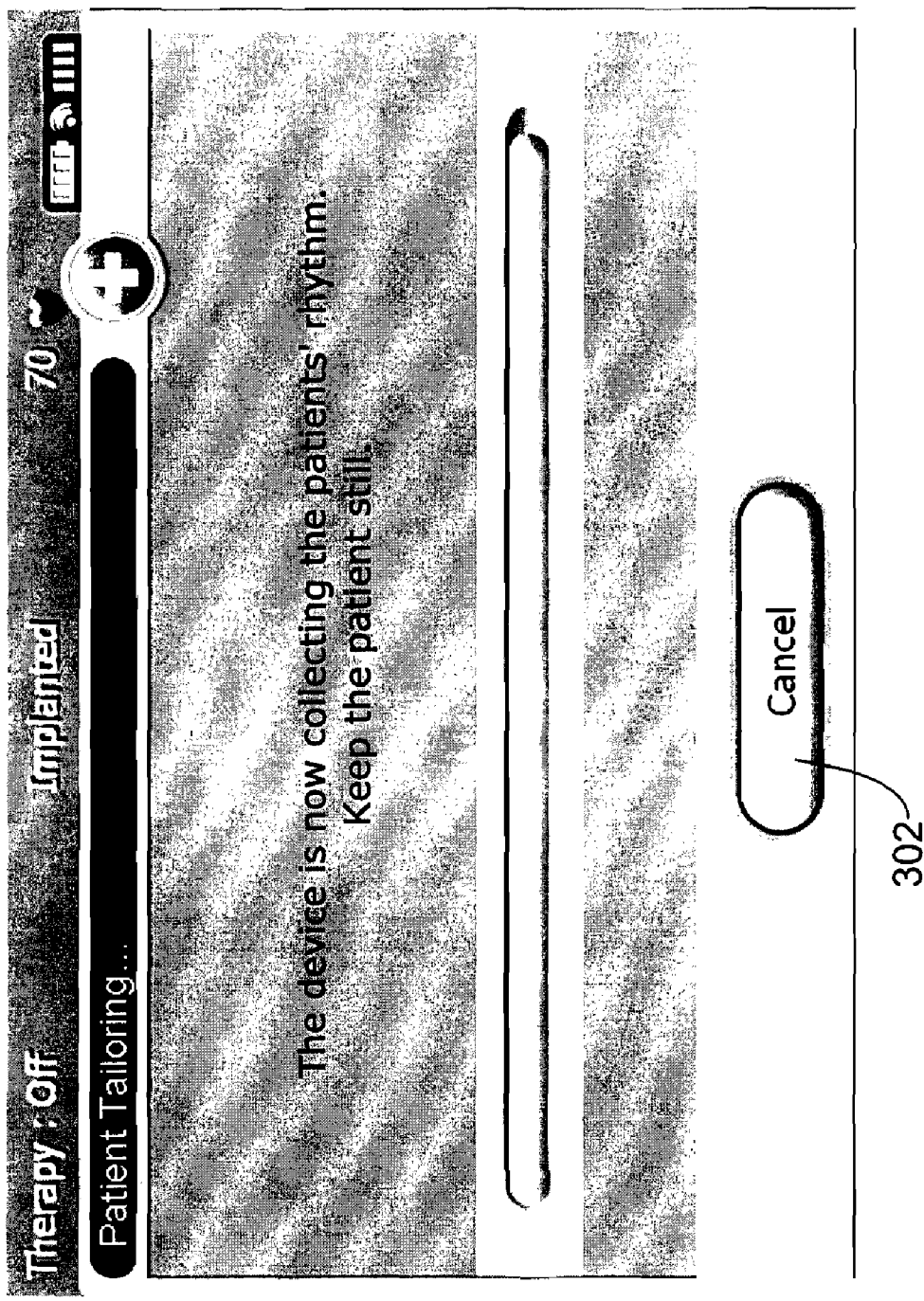

After the physician presses the "continue" icon 300 from the screen shot of FIG. 8A, the next screen that is seen is that of FIG. 8B, in which the programmer indicates that the device is collecting the patient's rhythm. The physician is requested to keep the patient still. A cancel icon 302 is provided in case the physician determines that the procedure should stop, for example, if the patient feels uncomfortable or ill, displays a physical abnormality (rising heart rate, for example), or if the patient moves. If desired, a status bar may be provided to indicate the progress of the sensing vector analysis to the physician.

Figure 8C:
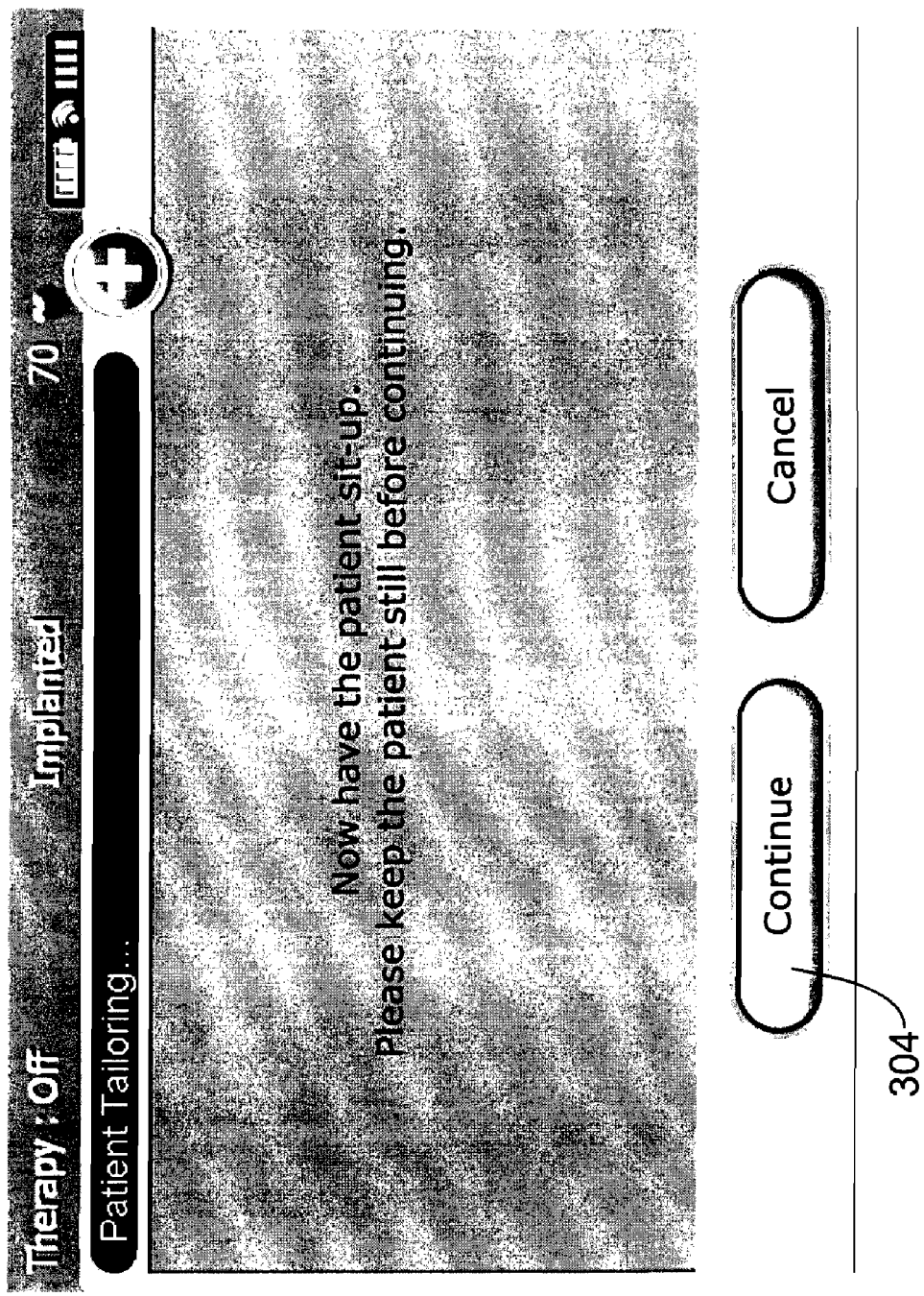
Figure 8D:
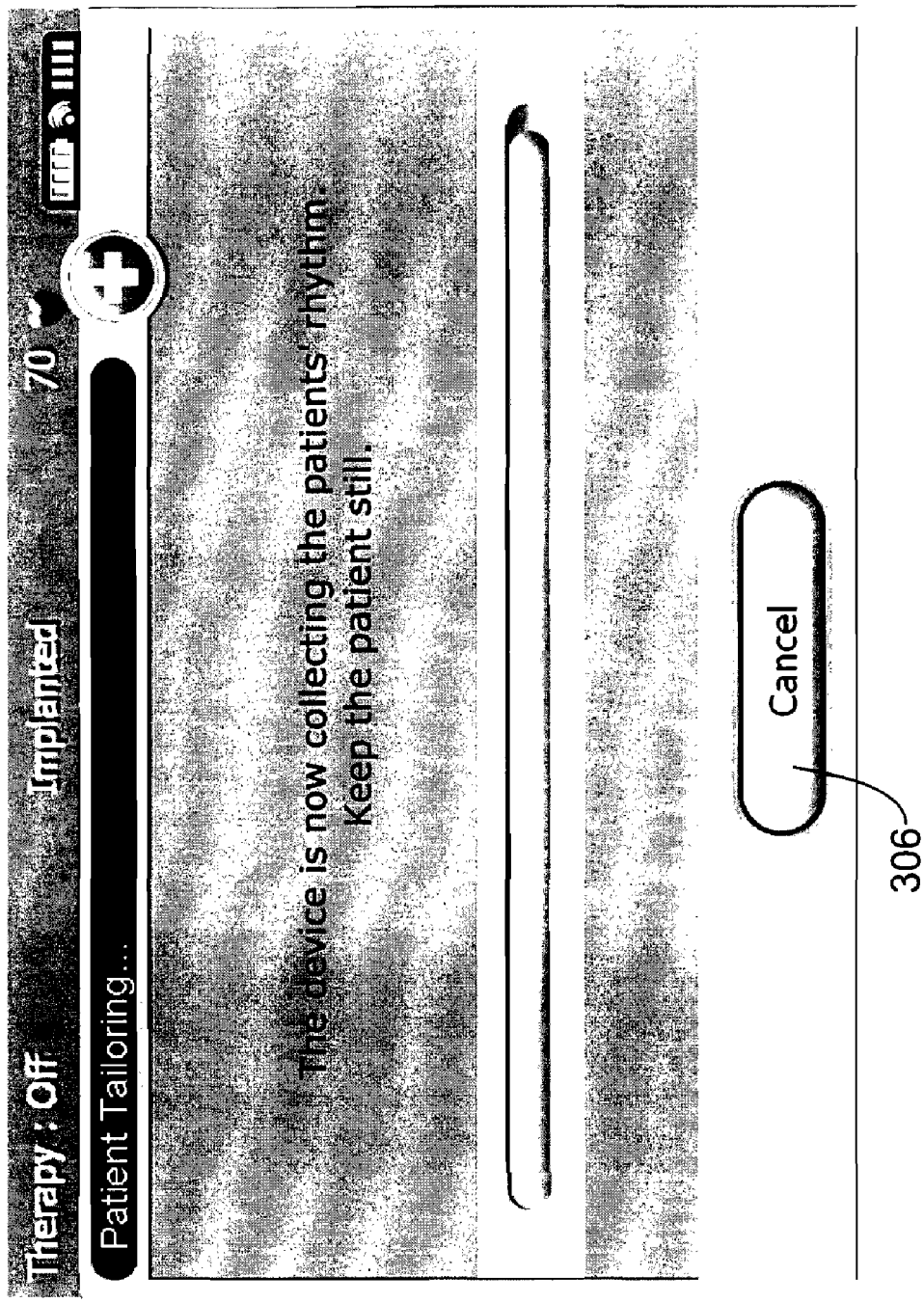

Once data is captured for the first patient body position, the next screen shot is that of FIG. 8C. The physician is asked to have the patient sit up (a second body position). With the patient sitting up, the physician is asked to keep the patient still and depress the continue icon 304. The programmer then displays the screen shot of FIG. 8D, which is quite similar to that of FIG. 8B and again includes an optional cancel button 306 and may include a status bar.

Figure 8E:
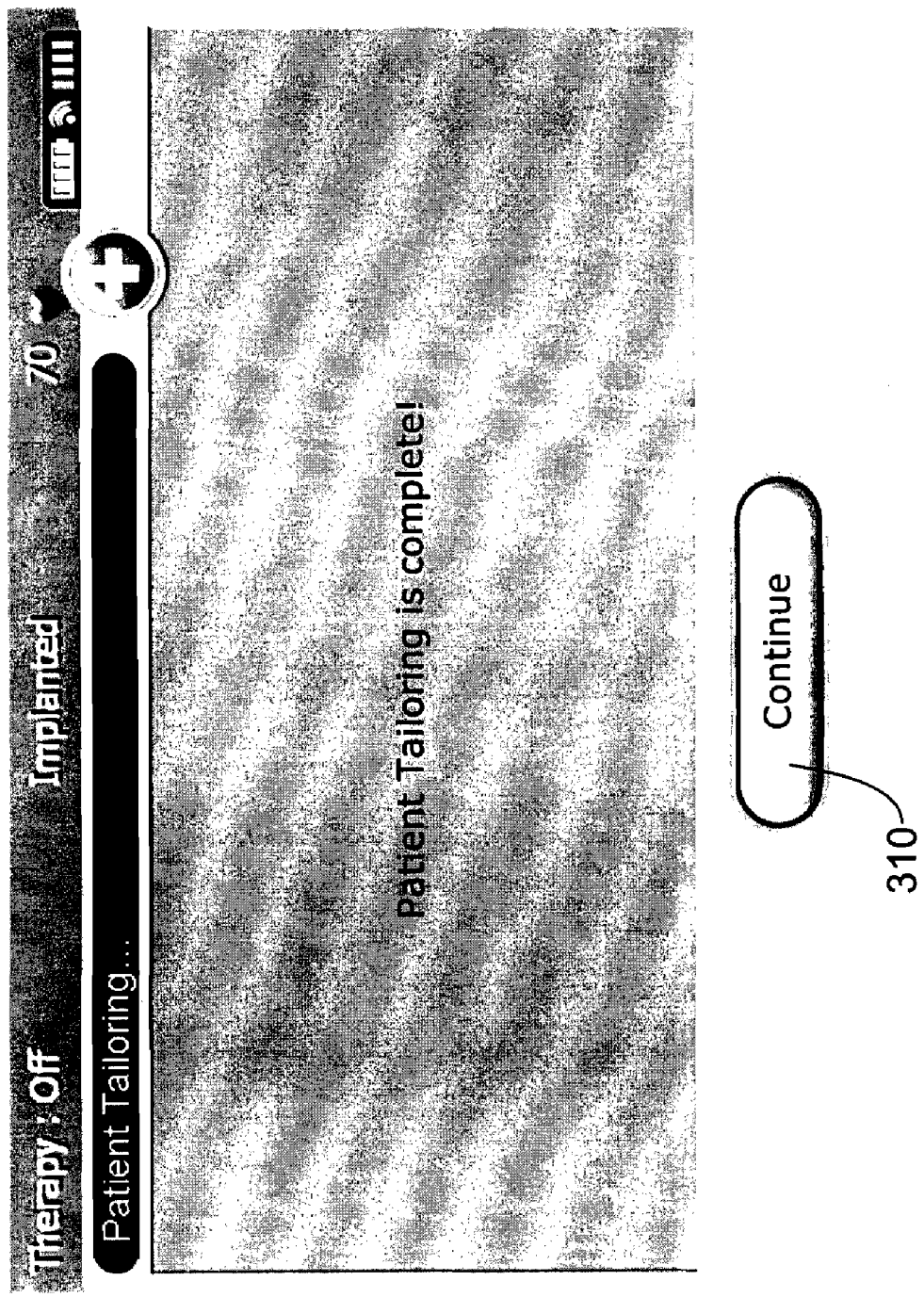

As shown in FIG. 8E, once data capture is complete for the second body position, patient tailoring in the illustrative embodiment is complete. The physician (or other operator)

may go on to perform other tasks by touching the "continue" icon 310. In other embodiments, additional data capture may ensue, if desired.

In some embodiments, the data capture for the patient may include options for physician input. For example, during data capture, it is possible for an artifact (such as a T-wave) to interfere with detection of R-waves. In some instances, the physician's input may be needed or requested to resolve any questions relating to event classification. Some examples are discussed in copending U.S. application Ser. No. 11/441,522, filed May 26, 2006 and entitled SYSTEMS AND METHODS FOR SENSING VECTOR SELECTION IN AN IMPLANTABLE MEDICAL DEVICE. In one illustrative embodiment, any such questions are delayed until all data has been captured, allowing the physician to concentrate on the programmer to answer such questions, rather than having the patient remain in a predetermined position while such issues are resolved. In another illustrative embodiment, such questions are asked as they arise.

In some embodiments, the above methods may be revisited later, after implantation, by the patient on his or her own. For example, as home-monitoring systems become available for patients with implanted cardiac monitoring and/or stimulus devices, a home monitoring system may be used to communicate with the implanted device, allowing later re-selection of sensing vectors in light of postural assessment. The home monitoring system, in an illustrative example, may include a graphical user interface allowing the user to indicate readiness for postural assessment, after which the home monitoring system may provide graphical output indicating what to do, physically, for the patient to complete home-monitoring self-assessment of postural effects on cardiac signals. Thus, a home monitoring system having functionality allowing it to provide patient directions in support of postural assessment may also be a "programmer" in the methods and systems discussed herein.

Yet another illustrative embodiment may include a device as shown in either of FIGS. 1A-1B which includes a sensor or sensing system for determining patient body position. For example, the sensor may be a gravity sensor or accelerometer-type sensor. The sensor may also be used to measure transthoracic impedance as a surrogate for patient body position. In one embodiment, the system need not determine an actual position using the position sensor, but instead may identify position sensor output ranges that correlate to the usefulness of particular vectors and/or templates. For example, when a patient moves from sitting to standing, a position sensor output may indicate a change of position. When the position changes as indicated by the position sensor, the system may determine for itself whether the primary sensing vector should be changed by observing various template analyses. To this end, from the implanted medical device system perspective, knowledge of the position is not needed, but instead, identification of the best template from several that are available is sufficient.

During operation, another illustrative implanted medical device may periodically (at intervals) or occasionally (in response to a condition or request) perform postural assessment without requesting movement by the patient. For example, if the position sensor output is "X", vector selection may be performed. If the position sensor later provides a different output, "Y", vector selection may again be performed, as is may be presumed that the patient is in a different body position. This process may be repeated several times, with templates and vectors identified for various position sensor outputs. After the selection process, if the position sensor output returns to "X", then a vector and/or template associated with position sensor output "X" may be selected. Within this approach, a single vector may have multiple templates, each corresponding to a position sensor output.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of implanting a cardiac stimulus device in a patient comprising:
   physically implanting the cardiac stimulus device, including a canister and a lead system, into the patient, the canister and the lead system having a plurality of electrodes that, when implanted, define at least first and second sensing vectors;
   initializing the device, including activating the device such that the device captures signals along a sensing vector;
   directing the patient to assume at least first and second body positions to allow the implanted device to perform assessment of captured signals using at least the first and second sensing vectors; and
   selecting one of the at least first and second sensing vectors as a default sensing vector for monitoring cardiac activity of the patient regardless of the patient's body position;
   wherein the assessment of captured signals includes calculating a factor indicating a vector having less variation in signal quality across multiple postures, and the step of selecting one of the at least first and second sensing vectors includes selecting a vector in which sensing data captured in each position varies less than sensing data captured in each position in at least one other vector.

2. The method of claim 1, wherein selecting a default sensing vector comprises:
   capturing sensing data along at least the first and second sensing vectors while the patient is in the first body position;
   capturing sensing data along at least the first and second sensing vectors while the patient is in the second body position; and
   analyzing the captured sensing data.

3. The method of claim 2, wherein the step of selecting one of the sensing vectors as the default sensing vector includes selecting a vector using consideration of the following metrics:
   captured signal amplitude and noise amplitude for each vector in each position; and
   similarity of captured signal amplitude, for a given vector, in the first body position and the second body position.

4. The method of claim 2, wherein the step of selecting one of the sensing vectors as the default sensing vector includes determining whether a valid template can be formed for performing beat comparison between a captured beat and a formed template.

5. The method of claim 4, wherein the step of determining whether a valid template can be formed includes:
   capturing a series of detected events, wherein a detected event occurs when a captured signal amplitude crosses an event threshold and a detected event includes a number of samples related to the threshold crossing; and
   determining whether the series of detected events demonstrate similarity to one another.

6. The method of claim 1 wherein:
   the step of physically implanting the housing and the lead electrode assembly into the patient is part of a surgical procedure and includes emplacing the housing and lead electrode assembly in the patient using one or more incisions;

the step of initializing the device is performed during the surgical procedure that includes the step of physically implanting;

the surgical procedure includes closing the one or more incisions; and the step of directing the patient to assume at least first and second body positions is performed following completion of the surgical procedure but before the patient is discharged following surgery.

7. The method of claim 1 wherein:

the implantable cardiac stimulus system is configured for telemetric communication with a programmer;

the programmer includes means for communicating with a user of the programmer; and the programmer is configured to communicate to a user to the programmer and instruct the user to direct the patient in the step of directing the patient to assume at least first and second body positions.

8. The method of claim 7 wherein the programmer uses telemetric communication with the implantable cardiac stimulus system as part of the step of initializing the device.

9. The method of claim 7 wherein the programmer coordinates the analysis of at least the first and second sensing vectors while the patient holds the first and second body positions.

* * * * *